US010529444B1

(12) United States Patent
Zhou et al.

(10) Patent No.: US 10,529,444 B1
(45) Date of Patent: Jan. 7, 2020

(54) SYSTEM THAT RAPIDLY GENERATES A SOLVENT-EXCLUDED SURFACE

(71) Applicant: Nanome Inc., North Hollywood, CA (US)

(72) Inventors: Yang Zhou, San Diego, CA (US); Vincent Brunet, Sevres (FR); Kai Wang, San Diego, CA (US); Steven McCloskey, San Diego, CA (US)

(73) Assignee: Nanome Inc., North Hollywood, CA (US)

( * ) Notice: Subject to any disclaimer, the term of this patent is extended or adjusted under 35 U.S.C. 154(b) by 0 days.

(21) Appl. No.: 16/269,423

(22) Filed: Feb. 6, 2019

(51) Int. Cl.
*G06F 19/00* (2018.01)
*G16C 60/00* (2019.01)
*G06F 17/50* (2006.01)

(52) U.S. Cl.
CPC ......... *G16C 60/00* (2019.02); *G06F 17/5009* (2013.01)

(58) Field of Classification Search
CPC ............... G06F 16/285; G06F 16/9024; G06F 16/9535; G06F 17/5009; G06F 3/0418; G06F 17/5018; G06F 9/455; G06F 9/45504; G06F 9/45516; G16B 20/00; G16B 50/00; G16B 15/00; G16B 40/00; G16B 25/00; G16B 45/00; G16B 5/00; G16B 35/00; G01R 33/5608; G06K 9/46; G06K 9/82; G06T 7/50; G01B 7/345; G16C 10/00; G16C 20/50; G16C 20/80
See application file for complete search history.

(56) References Cited

U.S. PATENT DOCUMENTS

| | | | | |
|---|---|---|---|---|
| 9,721,380 | B2* | 8/2017 | Schoenberg | G06T 15/40 |
| 2006/0069527 | A1* | 3/2006 | Numata | G06T 17/10 |
| | | | | 702/168 |
| 2014/0104270 | A1* | 4/2014 | Schlei | G06T 17/00 |
| | | | | 345/419 |
| 2014/0222384 | A1* | 8/2014 | Nordmark | G06F 17/5018 |
| | | | | 703/1 |

(Continued)

OTHER PUBLICATIONS

Decherchi, S. et al. A general and robust ray-casting-based algorithm for triangulating surfaces at the nanoscale. PLOS One (Apr. 2013) vol. 8, Issue 4, e59744.*

(Continued)

*Primary Examiner* — Mary K Zeman
(74) *Attorney, Agent, or Firm* — ARC IP Law, PC; Joseph J. Mayo

(57) ABSTRACT

System that generates the solvent-excluded surface (SES) of a molecule using a parallel algorithm that may execute on a GPU. Parallel execution allows a SES to be created in seconds even for a large protein, or to be recreated rapidly when exploring modifications to molecular structure. The algorithm calculates a spatial field that represents a signed distance between an atom-facing surface of a probe and each point in 3D grid. Spatial field calculations for different grid points may be performed in parallel. The SES is then obtained as the zero isosurface of the spatial field, using for example marching cubes. Atoms and probes may be placed into spatial buckets and indexed by bucket to improve efficiency by limiting calculations to atoms and probes in the proximity of a point.

20 Claims, 19 Drawing Sheets
(15 of 19 Drawing Sheet(s) Filed in Color)

(56) References Cited

U.S. PATENT DOCUMENTS

2016/0275703 A1* 9/2016 Mariampillai ............ A61B 6/03
2017/0256048 A1* 9/2017 Flessner ................ G06T 7/0004

OTHER PUBLICATIONS

D'Agostino et al. CUDA accelerated molecular surface generation (published online Aug. 15, 2013) Concurrency and computation : practice and experience. vol. 26 pp. 1819-1831.*

Bajaj, et al. An adaptive grid based method for computing molecular surfaces and properties. ResearchGate Nov. 3, 2006.*

Lorenson, E. et al. Marching Cubes: a high resolution 3D surface construction algorithm. Jul. 1987, Computer Graphics vol. 21, No. 4 pp. 163-169.*

Lindow et al. Accelerated visualization of dynamic molecular surfaces. 2010. IEEE-VGTC Symposium on Visualization 2010. vol. 29 No. 3, pp. 943-952.*

Quan, C et al. Mathematical analysis and calculation of molecular surfaces. Jul. 2016, Journal of Computational Physics vol. 322 pp. 760-782.*

Krone et al. Fast visualization of Gaussian Density Surfaces for Molecular Dynamics and Particle System Trajectories. Eurographics Conference on Visualization (2012) Short Papers, p. 1-5.*

Hao et al. Geometry-guided computation of 3D electrostatics for large biomolecules. Computer Aided Geometric Design, 2006, vol. 23 p. 545-557.*

Andrei et al. Intuitive representation of surface properties of biomolecules using BioBlender. BMC Bioinformatics (2012) vol. 13 (Suppl 4) S16 pp. 1-.*

Liu et al. ESES: software for Eulerian solvent excluded surface. Computational Chemistry (2017) vol. 38 No. 7 pp. 446-466.*

Connolly, Michael L., "Solvent-Accessible Surfaces of Proteins and Nucleic Acids", *Science*, New Series, vol. 221, No. 4612 (1983): 709-713.

* cited by examiner

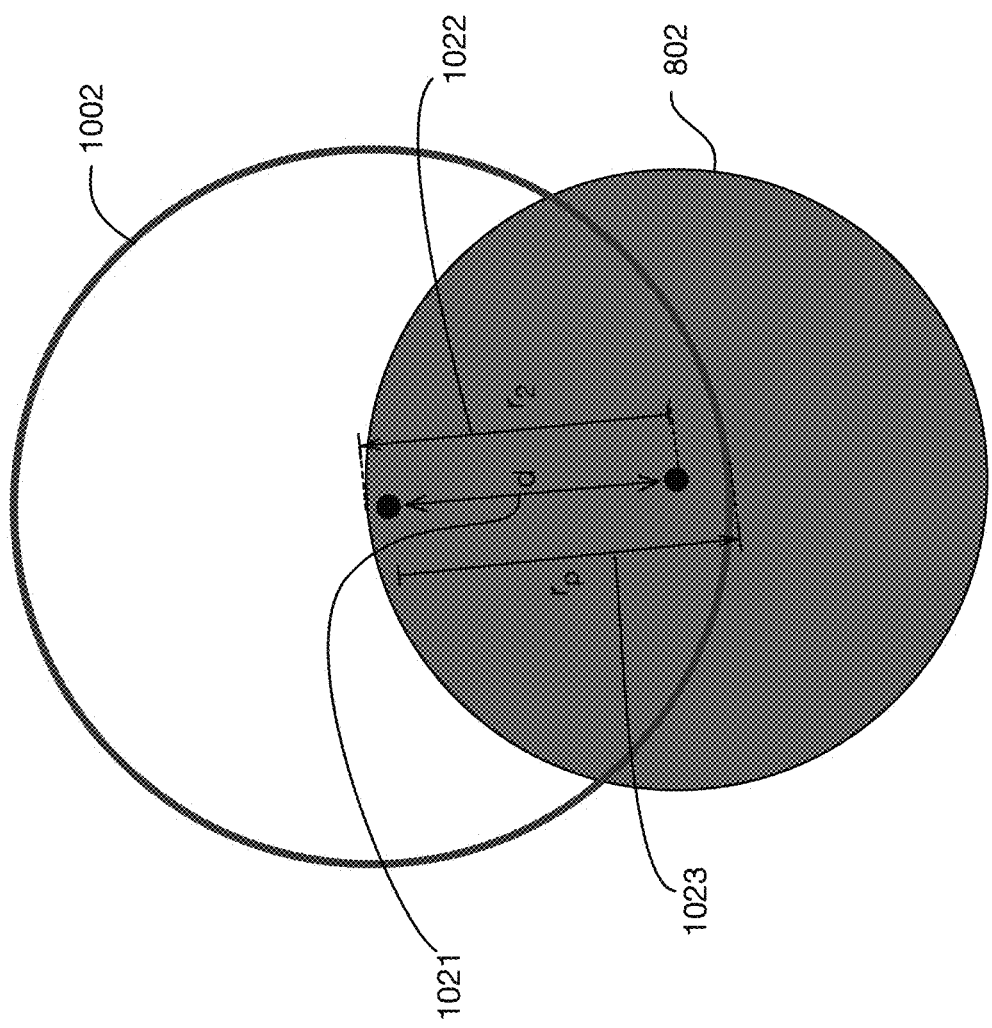

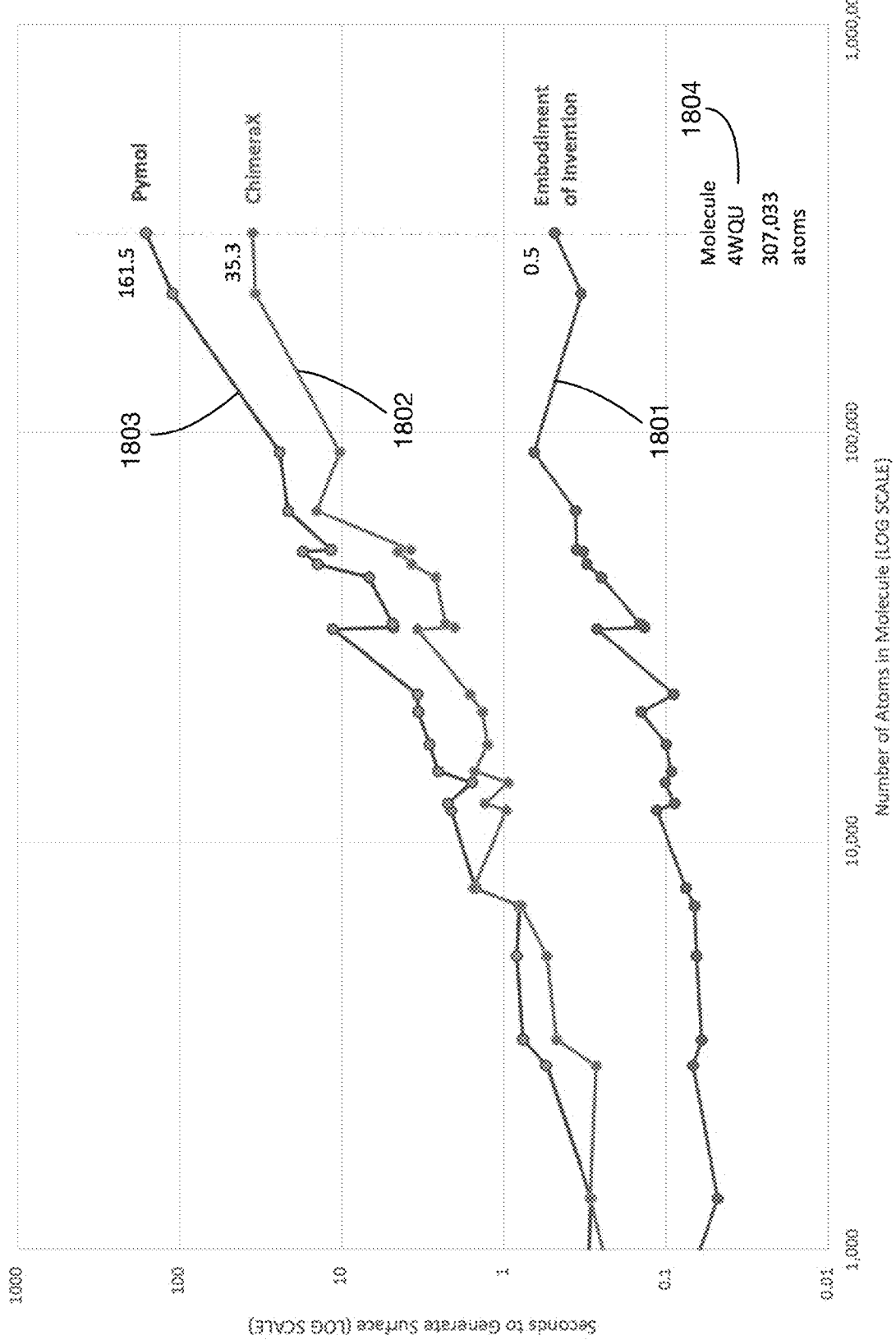

SYSTEM THAT RAPIDLY GENERATES A SOLVENT-EXCLUDED SURFACE

BACKGROUND OF THE INVENTION

Field of the Invention

One or more embodiments of the invention are related to the field of scientific visualization of molecules. More particularly, but not by way of limitation, one or more embodiments of the invention enable a system that rapidly generates a solvent-excluded surface.

Description of the Related Art

A solvent-excluded surface, also known as a Connolly surface, is a useful tool for molecular visualization, modeling, and simulation. This surface models the volume occupied by a molecule in a solvent if solvent molecules approach as closely as possible to the atoms of the molecule. The solvent is often taken to be water.

Methods are known for calculating a solvent-excluded surface from a molecular model, including the original method described in Connolly, Michael L., "Solvent-accessible surfaces of proteins and nucleic acids," *Science* 221 4612 (1983): 709-13. A drawback of the known methods for calculating solvent-accessible surfaces is that they can be very slow for very large molecules, such as proteins with tens or hundreds of thousands of atoms. The known methods are primarily sequential algorithms that do not take advantage of modern highly parallel processors such as GPUs. While surfaces can be computed offline for some known molecules, researchers often want to model modifications to molecular structure and then see the effects of these modifications on the solvent-excluded surface. With current methods for calculating solvent-excluded surfaces, a long delay may be introduced between making a modification and updating the solvent-excluded surface.

For at least the limitations described above there is a need for a system that rapidly generates a solvent-excluded surface.

BRIEF SUMMARY OF THE INVENTION

One or more embodiments described in the specification are related to a system that rapidly generates a solvent-excluded surface. The solvent-excluded surface may be calculated using a highly parallelizable algorithm that may execute largely on a GPU; parallel execution enables calculation or recalculation of the surface to be performed rapidly in comparison with sequential methods.

One or more embodiments may incorporate or use computer hardware including a processor with an attached memory and display. The processor may be configured to obtain a 3D model of a molecule, obtain a probe radius (which represents a solvent), and calculate the solvent-excluded surface of the molecule. The 3D model of the molecule may contain descriptions of the atoms of the molecule, including the location of their centers and their radii. Calculation of the solvent-excluded surface may generate a collection of probes around each atom. For each atom, these probes may be centered at vertices on a sphere around the atom's center with a radius equal to the atom radius plus the probe radius. Each probe may be represented at a sphere with a radius equal to the probe radius. The system may test each probe for whether it intersects any atom at more than one point, and if so that probe may be removed from the final probe list. The system may then calculate the value of a spatial field at points of a 3D grid that covers a volume (such as a bounding box) that contains the atoms and the final probes. This value may represent a minimum signed distance from each grid point to the atom-facing portion of a probe surface. The sign of this value may be different on the atom-facing side, which includes atom centers, and the probe-facing side, which include probe centers. The solvent-excluded surface may then be calculated as the zero isosurface of this spatial field. In one or more embodiments the processor may then display the solvent-excluded surface on the display.

The vertices used for generation of probes may be for example vertices of an icosphere centered at an atom center.

In one or more embodiments the zero isosurface of the spatial field may be calculated using a marching cubes algorithm.

In one or more embodiments the processor may groups atom into spatial buckets; this may improve efficiency of the calculations. To test whether a probe intersects an atom in more than one point, the system may identify the spatial bucket containing the probe center, identify a group of spatial buckets equal to or near this bucket, retrieve the atoms in that group of spatial buckets, and test for intersection of the probe with those atoms.

Calculating the value of the spatial field at a grid point may for example incorporate three steps in one or more embodiments. In the first step, the system may calculate a first value that is the minimum of the distance between the grid point and an atom center less the atom radius less the probe radius. This first value is an indication of whether a grid point is on the atom-facing side of a probe or on the side of a probe facing away from an atom. In the second step, the system may calculate a second value that is the minimum distance between the grid point and the centers of the final probes, less the probe radius. This second value is an indication of whether a grid point is inside a probe or is outside all probes. In the third step, the spatial field value may be set based on the sign of the first value: if the first value is negative or zero, the spatial field value may be set to the second value; if the first value is positive, the spatial field value may be set to the negative of the sum of the second value and twice the probe radius.

In one or more embodiments, the processor may group both atoms and the final probes into spatial buckets. The calculation of the first value may identify spatial buckets equal to or near the bucket containing a grid point, and may minimize the first value only over atoms in those spatial buckets. Similarly, the calculation of the second value minimize the second value only over probes in those spatial buckets.

In one or more embodiments, the processor may contain or may be coupled to a parallel processing unit, such as a GPU for example, that can execute computational tasks in parallel. Several of the calculations described above may be parallelized on this parallel processing unit. For example, the test of whether a probe intersects any atoms may be performed in parallel over the set of probes, with a computational task executed for each probe in parallel with corresponding computational tasks for one or more other probes. As another example, the calculation of the spatial field value for each grid point may be performed in parallel over the set of grid points, with a computational task executed for each grid point in parallel with corresponding computational tasks for one or more other grid points.

One or more embodiments that include a parallel processing unit may also perform parallel processing to generate the zero isosurface of the spatial field. The volume containing the molecule and the probes may be partitioned into cells, and a computational task may be generated for each cell to determine whether a portion of the zero isosurface passes through the cell, and if so to determine this portion. The computational task for a cell may be executed in parallel with corresponding computational tasks for one or more other cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other aspects, features and advantages of the invention will be more apparent from the following more particular description thereof, presented in conjunction with the following drawings wherein:

FIG. 10C illustrates a method to determinate whether two spheres intersect.

FIG. 18 shows a chart of performance benchmarks comparing the time to generate solvent-excluded surfaces between an embodiment of the invention and two commonly used molecular visualization systems.

DETAILED DESCRIPTION OF THE INVENTION

A system that rapidly generates a solvent-excluded surface will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
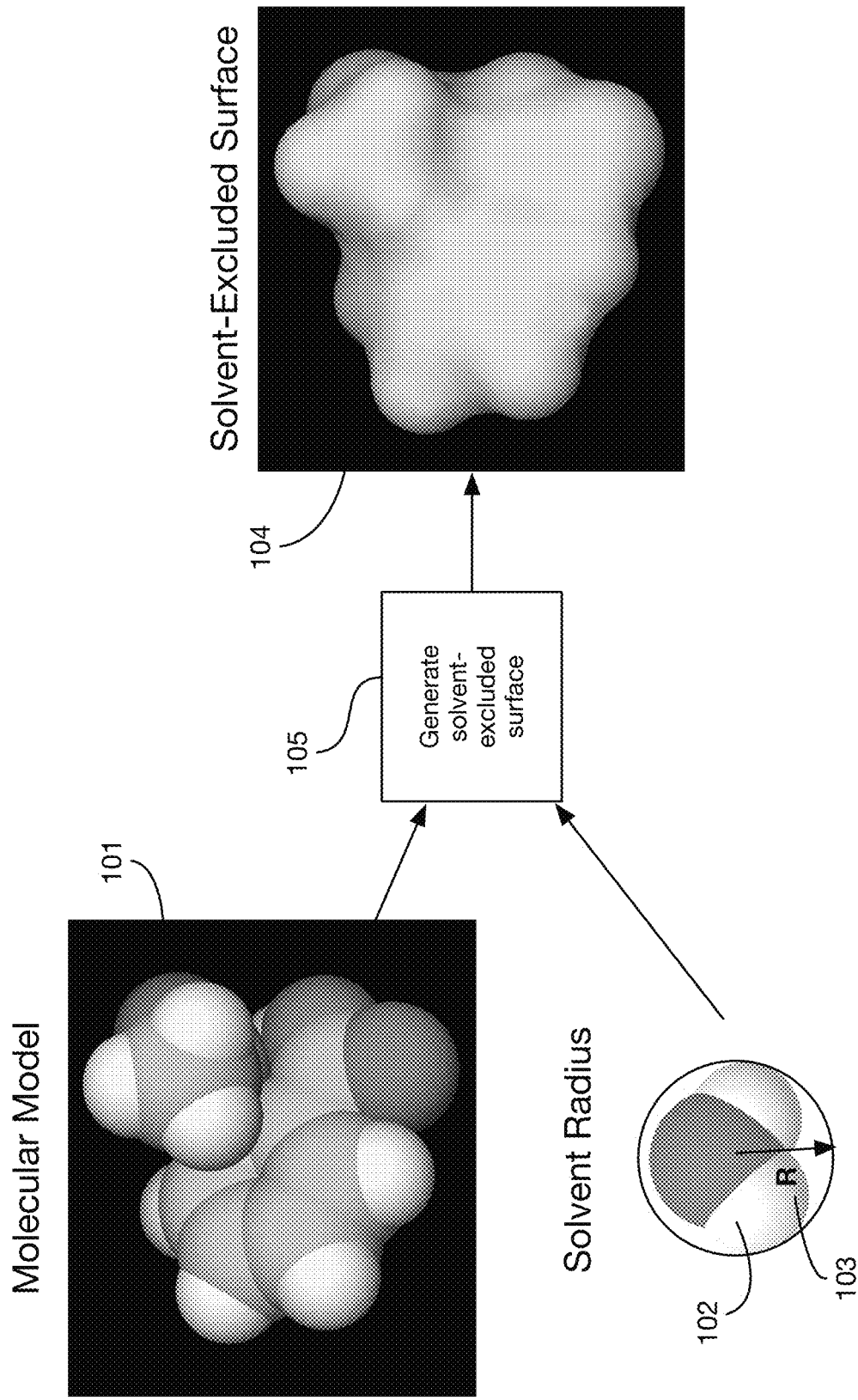
FIG. 1 shows illustrative inputs—a molecular model and a solvent model—and output—a solvent-excluded surface—of one or more embodiments of the invention.

FIG. 1 illustrates an overview of the inputs and output of one or more embodiments of the system. The system may obtain or create a molecular model 101. This model may for example describe the positions and sizes of the atoms in the molecule. The "molecule" in some situations may be multiple molecules that are considered as a unit for purposes of calculating a surface. While the molecule shown in FIG. 1 is extremely small for ease of illustration, in some applications embodiments of the invention may receive molecular models containing tens or hundreds of thousands of atoms, for example for large proteins. In addition to the molecular model 101, a model 102 of the solvent may also be received by or generated by the system. In many applications the solvent 102 may be water; however, one or more embodiments of the system may be used with any type of solvent. For surface calculations, it is common practice to simplify the solvent model to a single sphere with a solvent radius 103. This radius may be for example the van der Walls radius of the solvent.

Inputs 101 and 103 may be processed by system 105 to generate a solvent-excluded surface 104 of the molecule 101 with solvent 102. One or more embodiments may be used to generate other molecular surfaces using techniques similar to those described below. For example, without limitation, one or more embodiments may generate a solvent-accessible surface. One or more embodiments may also generate metrics associated with a surface, such as for example surface area.

Figure 2:
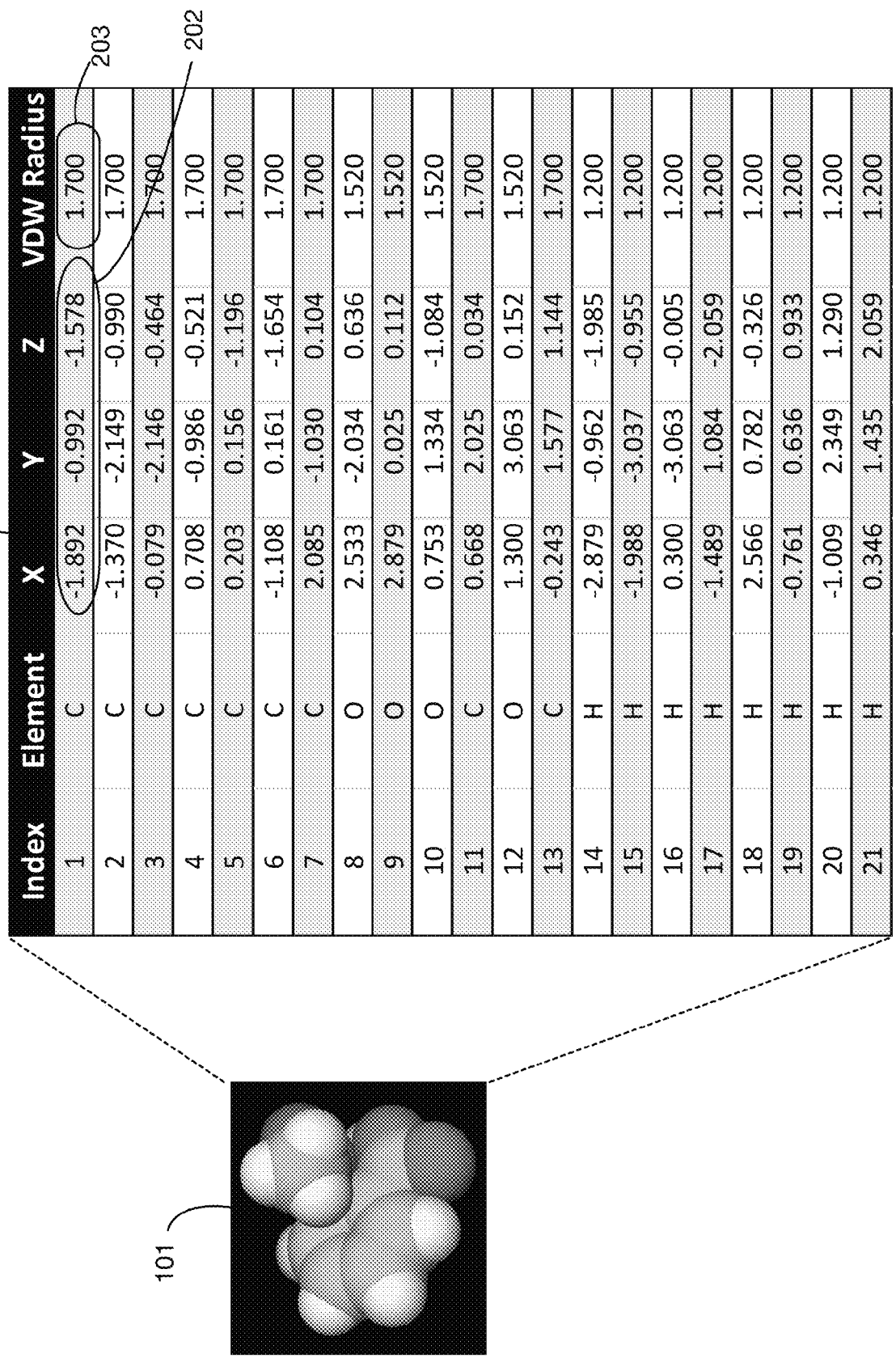
FIG. 2 shows illustrative data associated with a molecular model; one or more embodiments process this data to generate a solvent-excluded surface for the model.

FIG. 2 shows illustrative data 201 associated with molecular model 101. Each atom in model 101 may be described by a position 202 in 3D space, and by a radius 203 of the atom, which may be for example the atom's van der Walls radius. The position 202 may be measured with respect to a reference frame for the 3D model.

Figure 3:
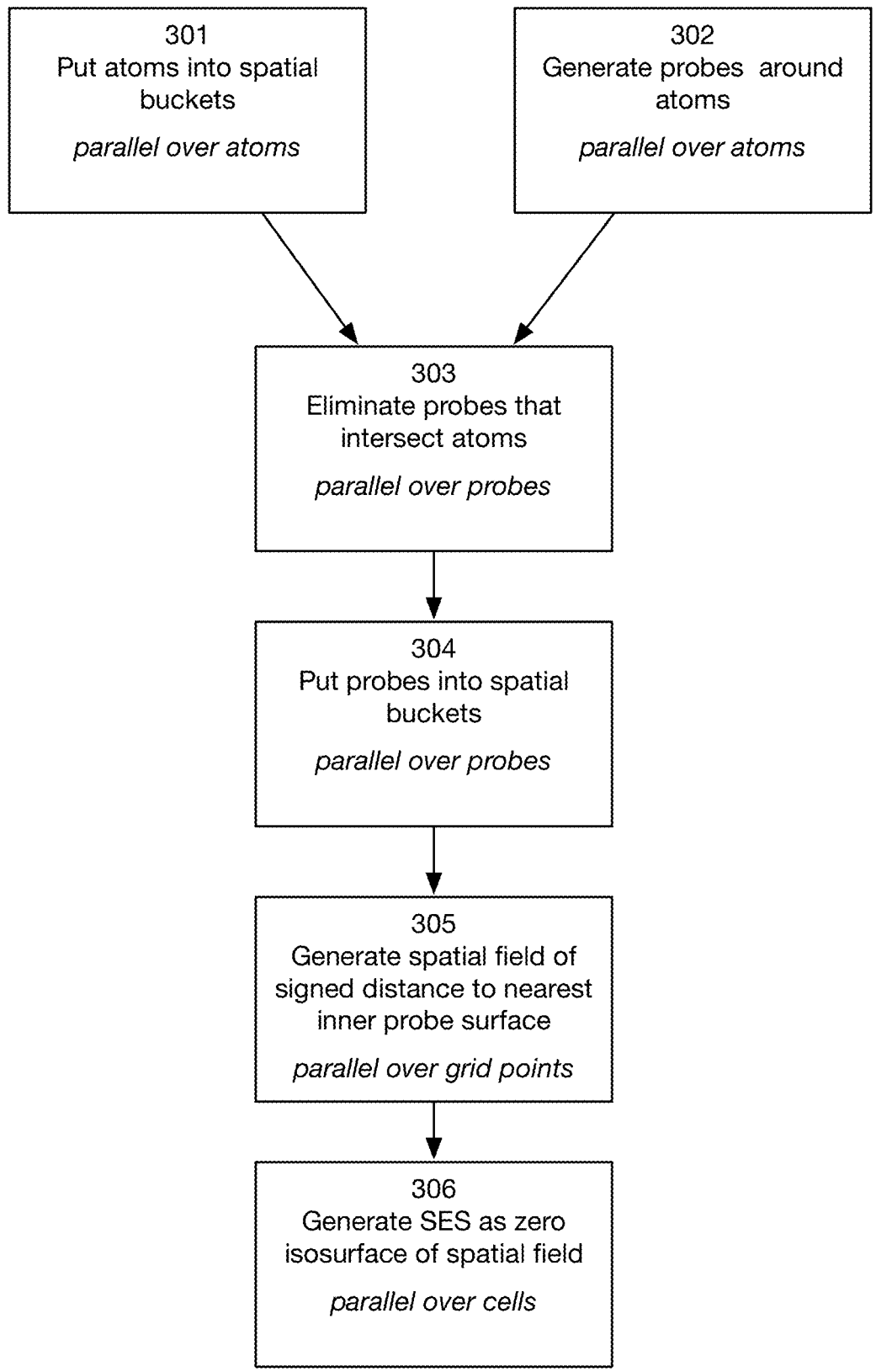
FIG. 3 shows a high-level flowchart of illustrative steps executed by one or more embodiments of the invention.

FIG. 3 illustrates high-level steps that may be performed by one or more embodiments of the system to transform inputs 101 and 103 into surface 104. One or more embodiments may perform these steps in different orders or may omit certain steps, add other steps, or combine certain steps. The dependencies shown among steps in FIG. 3 are also illustrative and may be modified in one or more embodiments.

Any or all of the steps shown in FIG. 3 may be parallelized, to execute fully or partially on a GPU for example. This parallelization may enable the system to generate a solvent-excluded surface rapidly, even for very large molecules. Rapid generation of the solvent-excluded surface may be particularly valuable in applications where a user is modifying a molecular model (for example during drug development), since the updated surface associated with a modified molecule may be calculated quickly. The parallelizability of significant portions of the processing performed by the system represents a benefit of the invention compared to existing sequential implementations of solvent-excluded surface calculations.

Each of the steps 301 through 306 will now be described briefly, with detailed descriptions provided below with respect to subsequent figures. Step 301 places atoms into spatial buckets, which increases processing efficiency by limiting calculations to atoms in the vicinity of a point. Parts of this step may be parallelized across atoms. Step 302 generates possible probes around each atom, which may also be performed in parallel across atoms. Step 303 checks the possible probes generated in step 302 for whether they intersect any atoms; if so, they are excluded since they do not contribute to the solvent-excluded surface. Step 303 may be performed in parallel across probes, and it may use the spatial buckets for atoms developed in step 301. Step 304 puts probes in spatial buckets, analogously to the placing of atoms in buckets in step 301. Step 305 generates a spatial field at grid points across the molecular model. Values of the spatial field may be calculated in parallel across grid points. The spatial field represents roughly a signed distance to the nearest inner probe surface. Finally, step 306 generates the solvent-excluded surface from the spatial field by locating the isosurface for the zero value of the field. Step 306 may be parallelized over cells (which have corners at grid points, for example).

Figure 4:
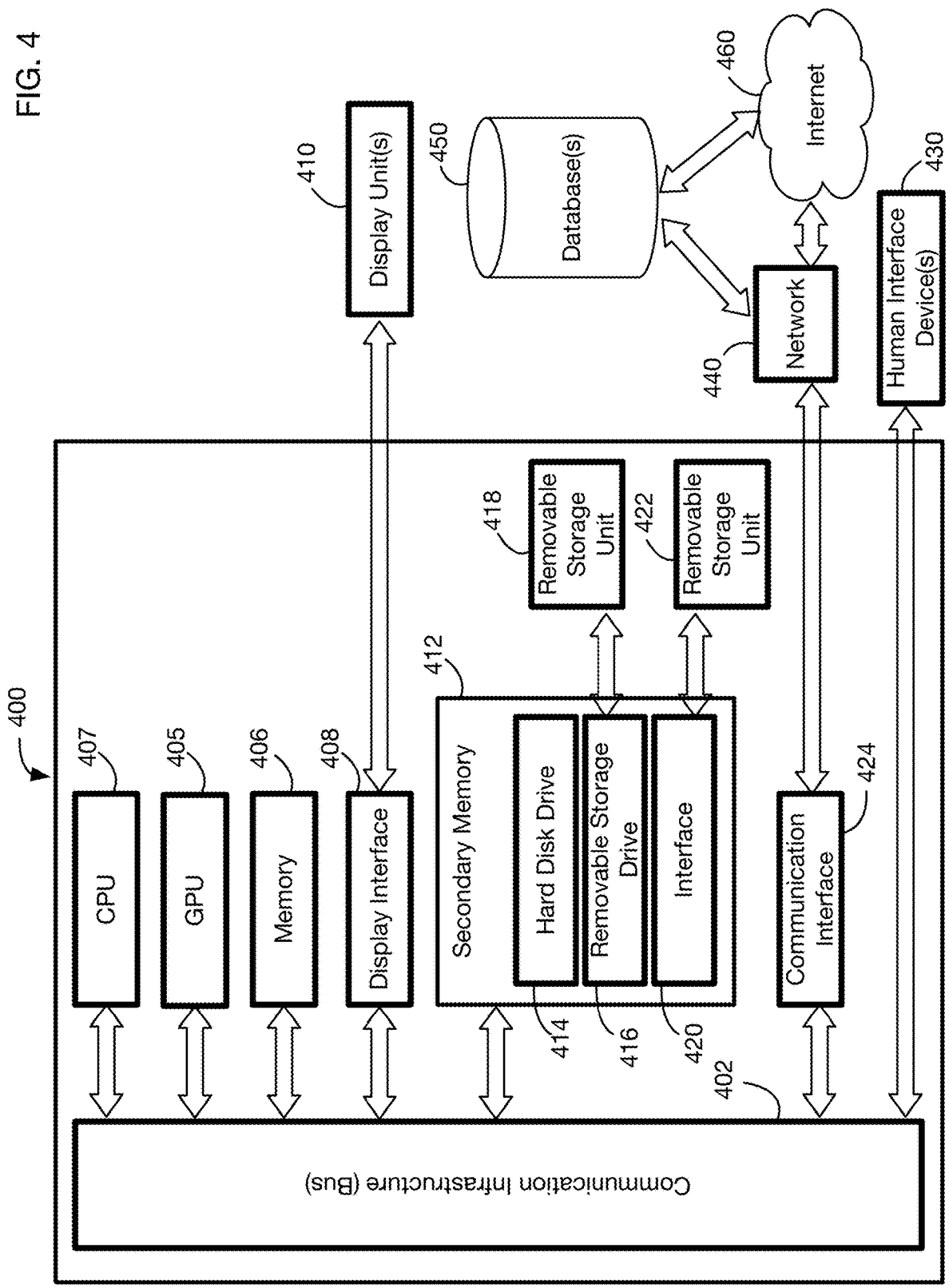
FIG. 4 shows a hardware architecture that may be utilized in one or more embodiments to execute the steps of FIG. 3.

The steps 301 through 306 are executed on one or more processors associated with one or more computers. FIG. 4 shows an architecture of illustrative computer hardware that may be used by or incorporated into one or more embodiments of the invention. The components shown in FIG. 4 are illustrative; one or more embodiments may use computers with other components, fewer components, or additional components. One or more embodiments may use or incorporate multiple computers, for example in a distributed system, to further accelerate processing; the parallelizability of the steps of FIG. 3 may also facilitate use of distributed processing.

FIG. 4 shows an embodiment of exemplary computer 400 that may be utilized in, by, or as any component in the system. In one or more embodiments, computer 400 may be a network of computers, each of which may have any or all of the components shown in FIG. 4. In one or more embodiments, computer or computers 400 may also be utilized to implement any function in the system, i.e., any step or act or function that executes in any computer or server or engine in the system. Computer 400 may include processor CPU 407 that executes software instructions specifically tailored to the respective functions of embodiments of the invention. The software instructions, otherwise known as computer program instructions, may reside within memory 406. Computer 400 may include processor GPU 405, which may execute graphics instructions or other instructions for highly parallel operations, for example. GPU program instructions may also reside within memory 406. Computer 400 may include display interface 408, which may drive display unit or units 410 of any computer in the system as desired. Some computers 400 may or may not utilize a display. Computer 400 may include communication interface 424, which may include wireless or wired communications hardware protocol chips. In one or more embodiments of the invention communication interface 424 may include telephonic and/or data communications hardware. In one or more embodiments communication interface 424 may include a Wi-Fi™ and/or BLUETOOTH™ wireless communications interface. Any wireless network protocol or type may be utilized in embodiments of the invention. CPU 407, GPU 405, memory 406, display interface 408, communication interface 424, human interface devices 430, secondary memory 412, such as hard disk 414, removable storage 416, secondary memory interface 420 and removable storage units 418 and 422 may communicate with one another over communication infrastructure 402, which is commonly known as a "bus". Communications interface 424 may communicate over any wired or wireless medium that allows for communication with other wired or wireless devices over network 440. Network 440 may communicate with Internet 460 and/or database or databases 450. Database 450 may be utilized to implement any database described herein.

Figure 5:
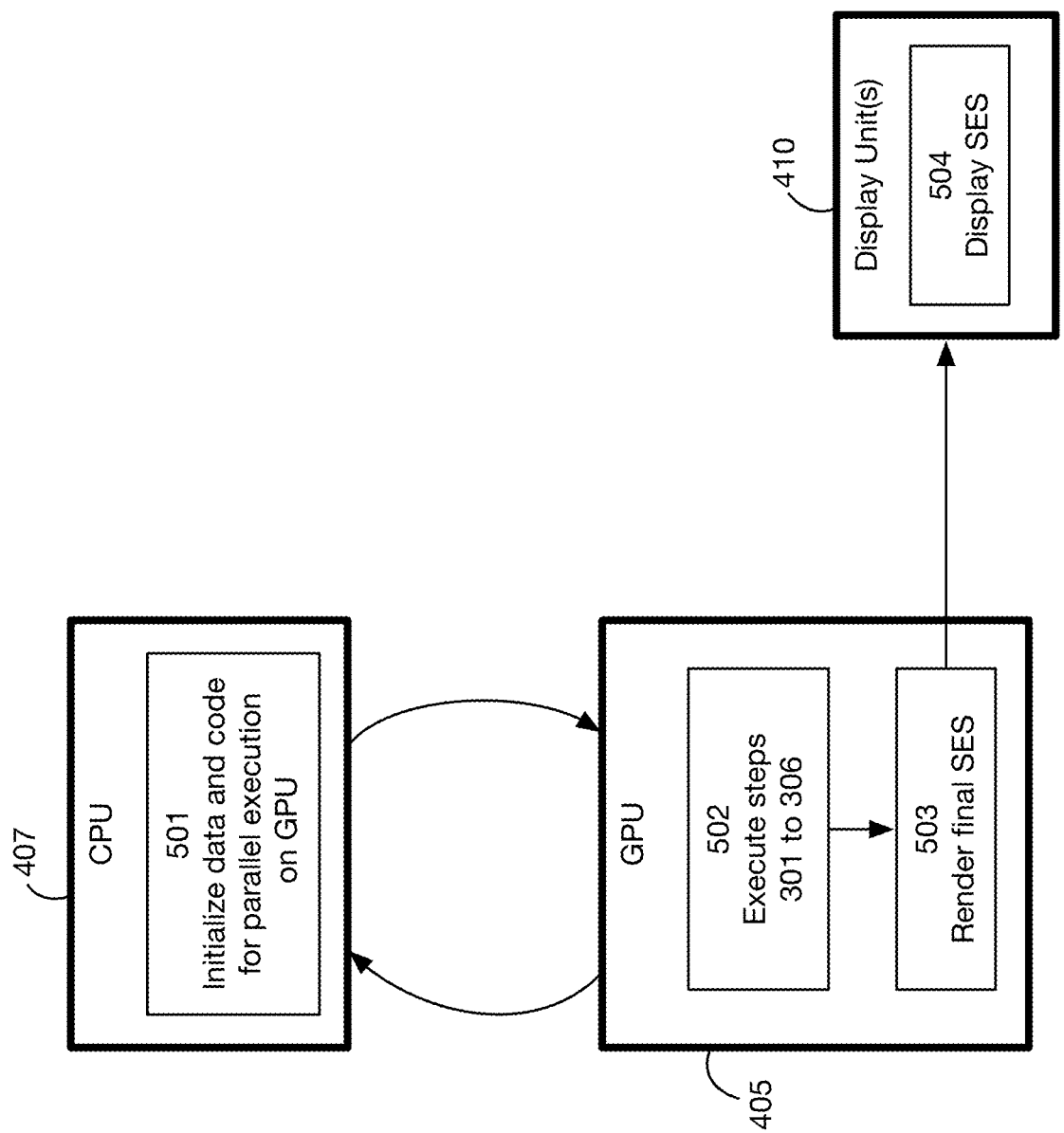
FIG. 5 shows illustrative parallelization of the steps of FIG. 3 using for example a GPU.

FIG. 5 shows how processing may be partitioned between CPU 407 and GPU 405 in one or more embodiments of the system. CPU 407 may perform steps 501 to initialize data and code for parallel execution on GPU 405. GPU 405 may perform steps 502 to execute steps 301 to 306 of FIG. 3. The multiple cores of the GPU may act in parallel on the various data units such as atoms, probes, grid points, or cells. For example, if a calculation needs to be performed for all atoms, and if this calculation has no interdependencies among atoms, then each core of the GPU may perform a calculation for one atom in parallel with the other cores performing this calculation for other atoms. Groups of atoms may be pipelined through the multiple cores if there are not enough cores to work on all atoms at once.

GPU 405 may then perform step 503 to render a final solvent-excluded surface. The final surface may be transmitted to display unit 410 for display step 504. The CPU and GPU may communicate throughout execution of steps 301 to 306. In one or more embodiments the display step 504 may be performed at a later time, or on another computer system; for example, one system may calculate the solvent-excluded surface and store it for later use or transmit it over a network to a client computer.

FIGS. 6 through 17 describe the steps 301 through 306 in more detail. In these figures, molecules, atoms, probes, spatial fields, are shown in two dimensions for ease of illustration, and "surfaces" are shown as two-dimensional curves. In application, molecular models and surfaces are typically three dimensional. The processes and algorithms described and illustrated in 2D may be implemented immediately in 3D with no fundamental changes (other than adding an additional dimension to the various spatial data structures). In general, in the descriptions below we refer to "spheres" and "surfaces" because these will be the three-dimensional objects used in practice in embodiments of the invention; however, these "spheres" and "surfaces" will be illustrated in the Figures as circles and curves in two dimensions.

Figure 6:
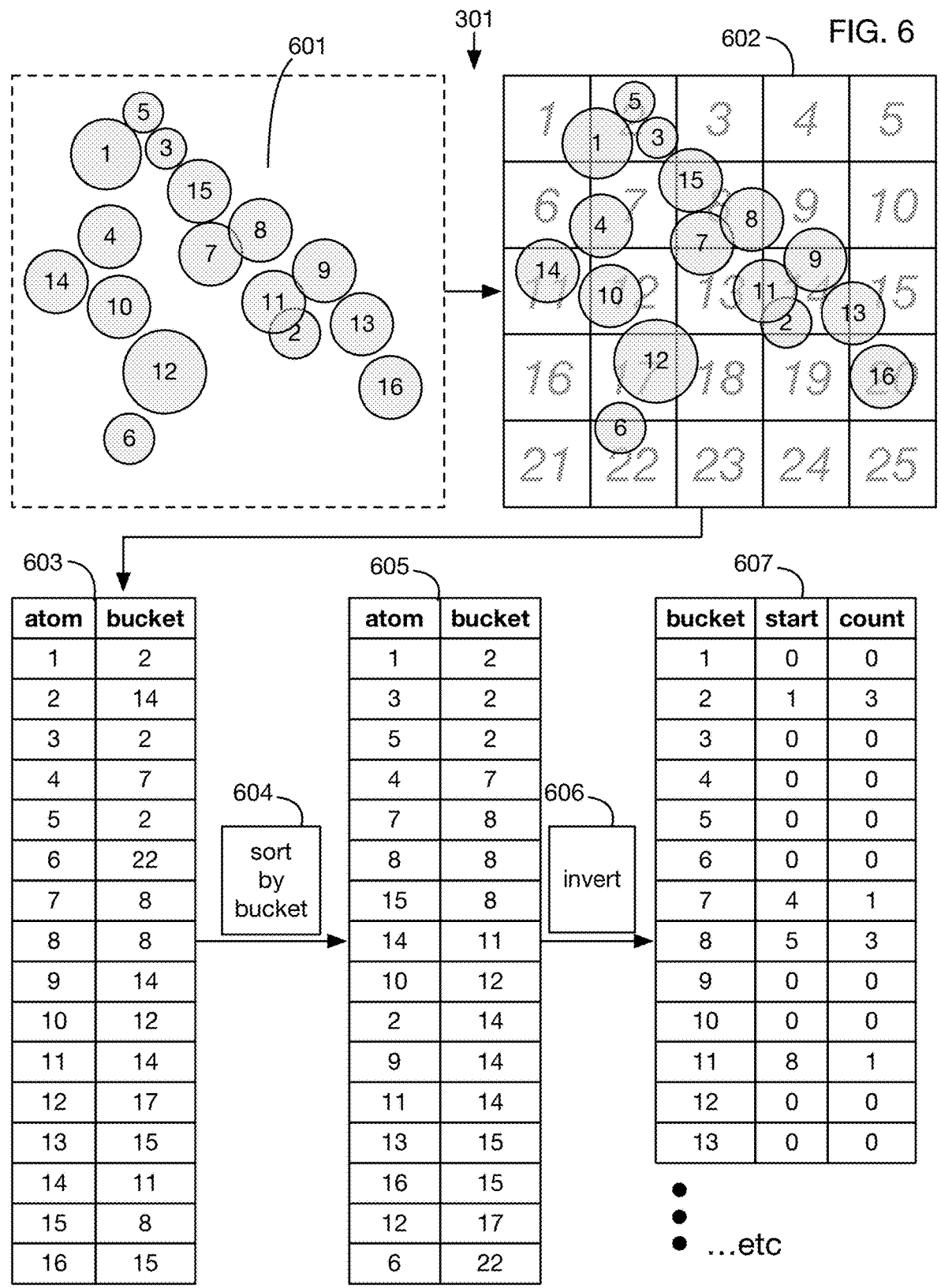
FIG. 6 shows an illustrative example of putting atoms into spatial buckets, which may make subsequent steps more efficient by limiting the number of atoms that need to be considered for a calculation.

FIG. 6 illustrates step 601, placing atoms into spatial buckets. Some of the steps described below involve calculation of distances between a point and the "closest" atom to the point. A naïve implementation involves calculation of distances to each atom, and selecting the smallest result. For large molecules, this approach may involve hundreds of thousands of distance calculations for each point. To reduce the number of calculations, one or more embodiments develop a spatial index so that the atoms nearest a point can be identified rapidly. Atoms 601 are overlaid with a grid of spatial buckets 602. Buckets may be of any desired size, and the grid may contain any number of buckets. Each atom may be mapped to the bucket containing the atom's center, resulting in list 603. Calculation of which bucket each atom is in is straightforward; for example, if the area spanned by bucket grid 602 is $[0,1]^2$, then an atom with center at (x, y) is in the bucket with index 1+int(5x)+5*int(5y). This calculation may be done in parallel for each atom on a GPU. List 603 may then be sorted in operation 604 by bucket index, resulting in sorted list 605. The sort may be performed for example on a GPU as a radix sort, or using any other sort algorithm. Finally, an inversion operation 606 may generate an index 607 that maps bucket indices into the sorted atom list 605, so that the atoms in a bucket may be quickly retrieved.

Figure 7:
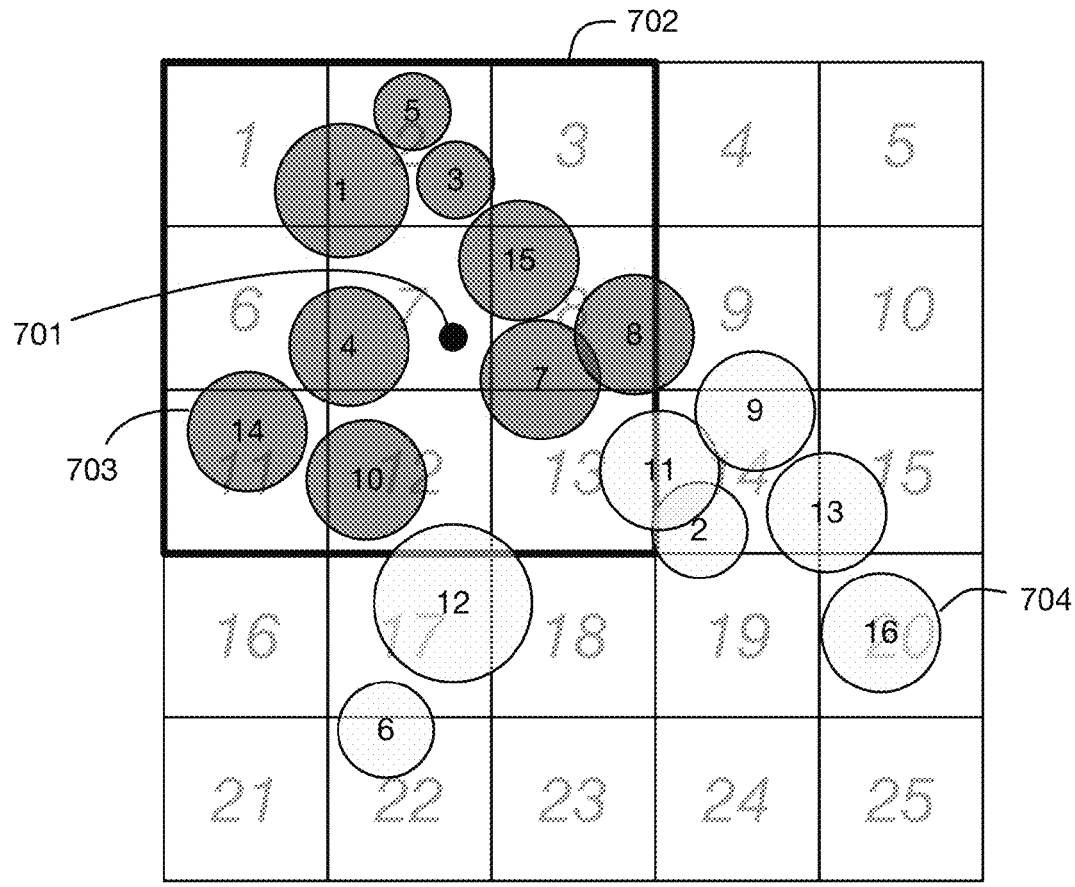
FIG. 7 illustrates how spatial bucketing of atoms may be used to limit the number of atoms considered.
Figure 7:
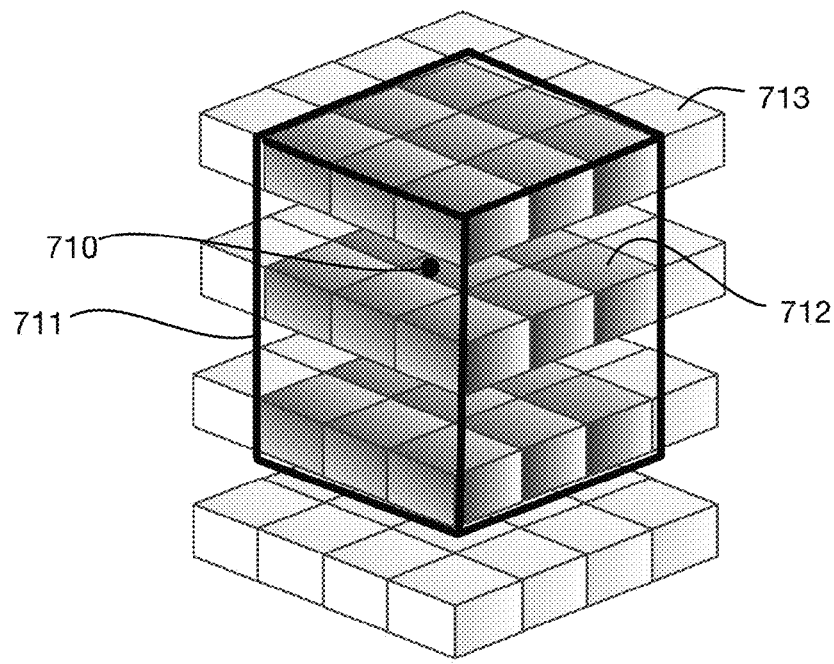

FIG. 7 illustrates how the bucket-to-atom mapping may be used in one or more embodiments. A calculation may involve for example distances between point 701 and nearby atoms. The bucket index of the point may be determined (here it is 7), and the buckets in the neighborhood of the point's bucket may be identified. For example, the neighborhood to be considered may be all buckets in the 3×3 subgrid 702 centered at the point's bucket. This 3×3 neighborhood is illustrative; one or more embodiments may search for atoms in any neighborhood around a point's bucket. The bucket indices of buckets in the subgrid 702 may be calculated directly from the index of the point's bucket. The atoms in these buckets may then be obtained from index 607 and sorted atom list 605. For example, atom 703 is determined to be in this neighborhood because it is in bucket 11.

The process of locating neighboring buckets is similar in three dimensions. For example, buckets in the neighborhood of point 710 may be the 3×3×3 subgrid 711, which includes bucket 712 but excludes bucket 713. The 3×3×3 neighborhood is illustrative; one or more embodiments may use any bucket neighborhood size, including for example a 1×1×1 neighborhood (which includes only the bucket containing the point) or a larger 5×5×5 neighborhood.

Figure 8B:
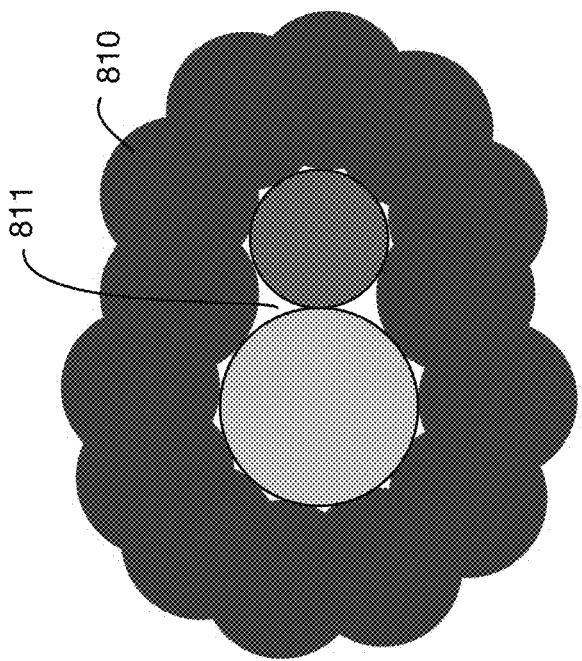
FIGS. 8A through 8C show an overview of the conceptual framework that defines a solvent-excluded surface.
Figure 8C:
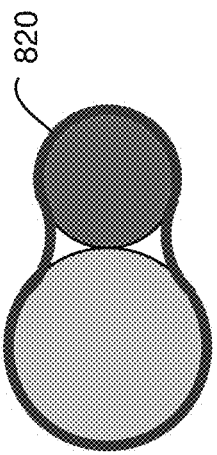
Figure 8A:
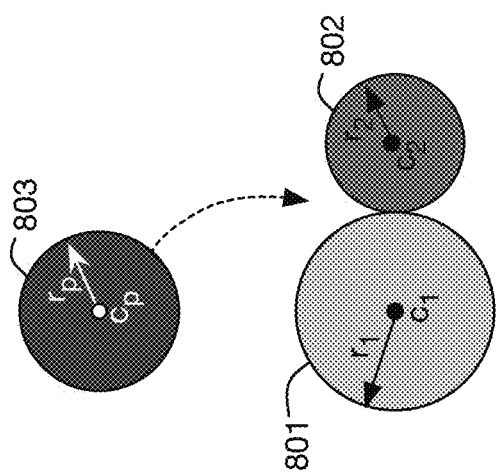

FIGS. 8A through 8C show a conceptual framework for defining the solvent-excluded surface around a molecule. For ease of illustration in these and subsequent figures, we use a simple two-atom molecule consisting of atoms 801 and 802, shown in FIG. 8A. The solvent-excluded surface is described by placing copies of a solvent 803, modeled as a sphere (shown as a circle in 2D) against the atoms 801 and 802. These copies are called "probes." This process is illustrated in FIG. 8B, which shows a "cloud" of probes 810 surrounding the molecule. Conceptually probe spheres may be in any position tangent to any of the atoms of the molecule, resulting in an infinite cloud of probes. FIG. 8B shows a sampling of these probe spheres at selected locations. The solvent-excluded surface is defined as the envelope of the inner surfaces of the probes. This surface 820 is shown in FIG. 8C. In the simple two atom molecule, portions of the solvent-excluded surface coincide with the outer surface of the atoms, but there is a gap 811 between the atoms that a probe cannot penetrate.

One or more embodiments of the system effectively recreate the process illustrated in FIGS. 8A through 8C by generating probes around atoms of the molecule and calculating an envelope of their inner surfaces. Instead of an infinite cloud of probes, embodiments generate a sampling of probe spheres at discrete locations around each atom. FIG. 9A shows illustrative probes generated around atoms 801 and 802. Every probe must be tangent to at least one atom in a molecule. For example, probe 903 is tangent to atom 801, and probe 905 is tangent to atom 802. A probe is tangent to an atom when the center of the probe lies on a sphere (shown as a circle in 2D) surrounding the atom center with a radius equal to the atom radius plus the probe radius. For example, the center 904 of probe 903 lies on sphere 901, and the center 906 of probe 905 lies on sphere 902. This observation leads to the technique illustrated in FIGS. 9B and 9C for generating possible probes: an "extended atom sphere" is generated around each atom, with a radius equal to the atom radius plus the probe radius, and probes are generated with centers on these extended atom spheres.

Figure 9B:
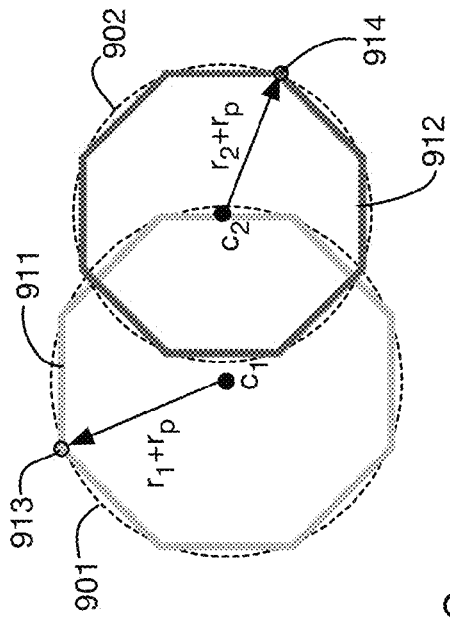
FIGS. 9A through 9C illustrate generation of probes around atoms.
Figure 9A:
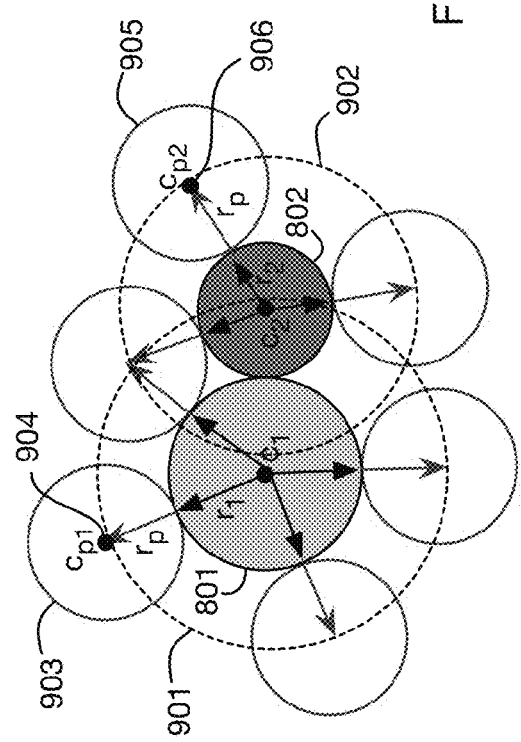

FIG. 9B shows an illustrative method of generating probe centers: a regular polygon is inscribed in the extended atom sphere around each atom, and probe centers are generated on the vertices of these polygons. In three dimensions, the regular polygons may be for example icospheres, or any type of polyhedra. One or more embodiments may use any method for sampling points on extended spheres around atoms to generate probe centers. In FIG. 9B, eight points per atom are generated by inscribing octagon 911 in sphere 901, and octagon 912 in sphere 902. Illustrative probe centers 913 and 914 are generated at vertices of these octagons. The use of polygons with 8 vertices is illustrative; one or more embodiments may use polyhedra (illustrated with polygons in 2D) with any number of vertices. A tradeoff in the selection of how many vertices to use around each atom is generating a smoother solvent-excluded surface with more vertices at the expense of more computation.

Figure 9C:
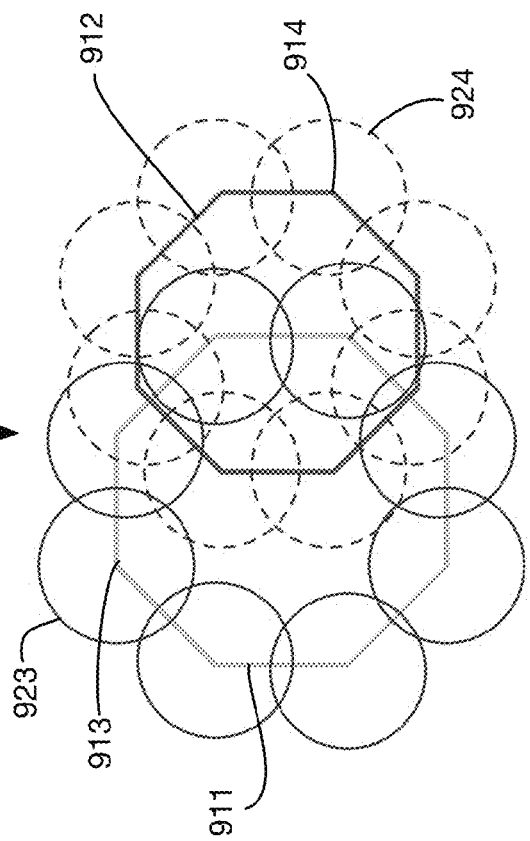

FIG. 9C shows the result of step 302 to generate the initial probes around each atom. In this illustrative example, shown in 2D, 8 probes are generated around each atom, for a total of 16 probes. For example, probe 923 is generated with a center at vertex 913 of octagon 911, and probe 924 is generated with a center at vertex 914 of octagon 912.

Figure 10B:
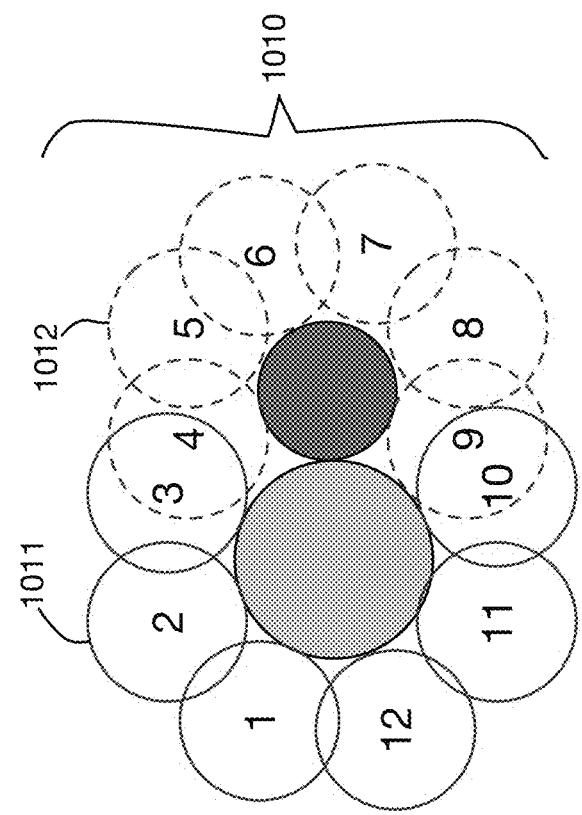
FIGS. 10A and 10B illustrate elimination of probes that intersect atoms.
Figure 10A:
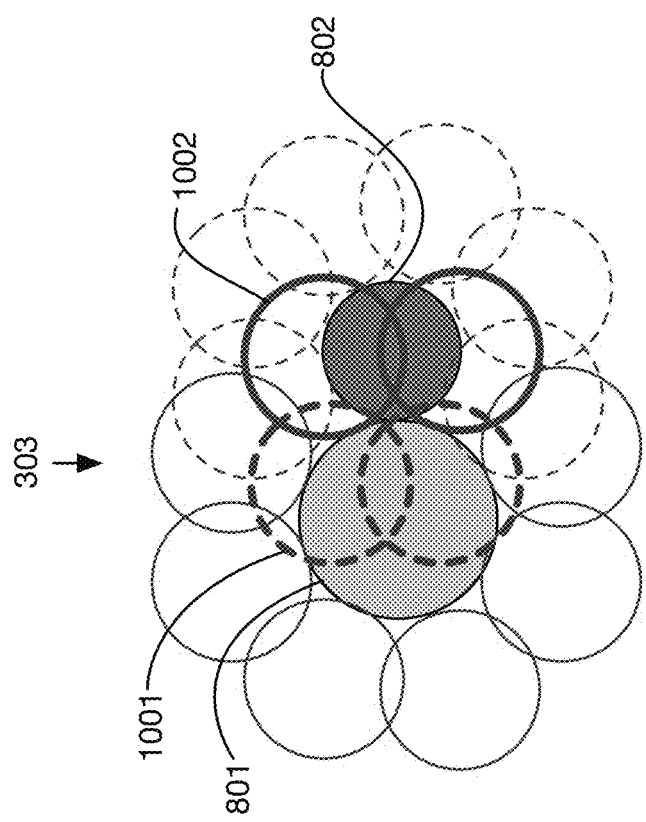

The next step 303 in one or more embodiments of the invention is to eliminate probes that intersect an atom at more than a single tangent point. FIG. 10A illustrates the probes from FIG. 9C overlaid onto atoms 801 and 802. Four of these probes intersect with atoms. For example, probe 1001 intersects with atom 801, and probe 1002 intersects with atom 802 (where "intersect" means intersecting at more than a single tangent point). These probes and two additional probes cannot represent solvent molecules on the surface of the molecule because they would imply that the solvent overlaps with an atom. Therefore, these intersecting probes are removed from the list of probes, leaving the final probes 1010 shown in FIG. 10B, such as probes 1011 and 1012.

Determining whether a probe and an atom intersect is a simple calculation, illustrated in FIG. 10C. The distance 1021 between the center of an atom 802 and the center of a probe 102 is compared to the sum of the atom radius 1022 and the probe radius 1023. If the distance 1021 is smaller than the sum of the radii 1022 and 1023, then the two spheres intersect at multiple points. This calculation may be performed for each probe and atom combination to check for intersections. However, the number of tests may be reduced by using the atom spatial buckets to locate atoms near each probe, and to check for probe intersections only with these atoms. The retrieval of atoms to check for each probe and the calculation of distances to test for intersection may be parallelized across probes, for example on a GPU, since the operations are independent across probes.

Figure 11:
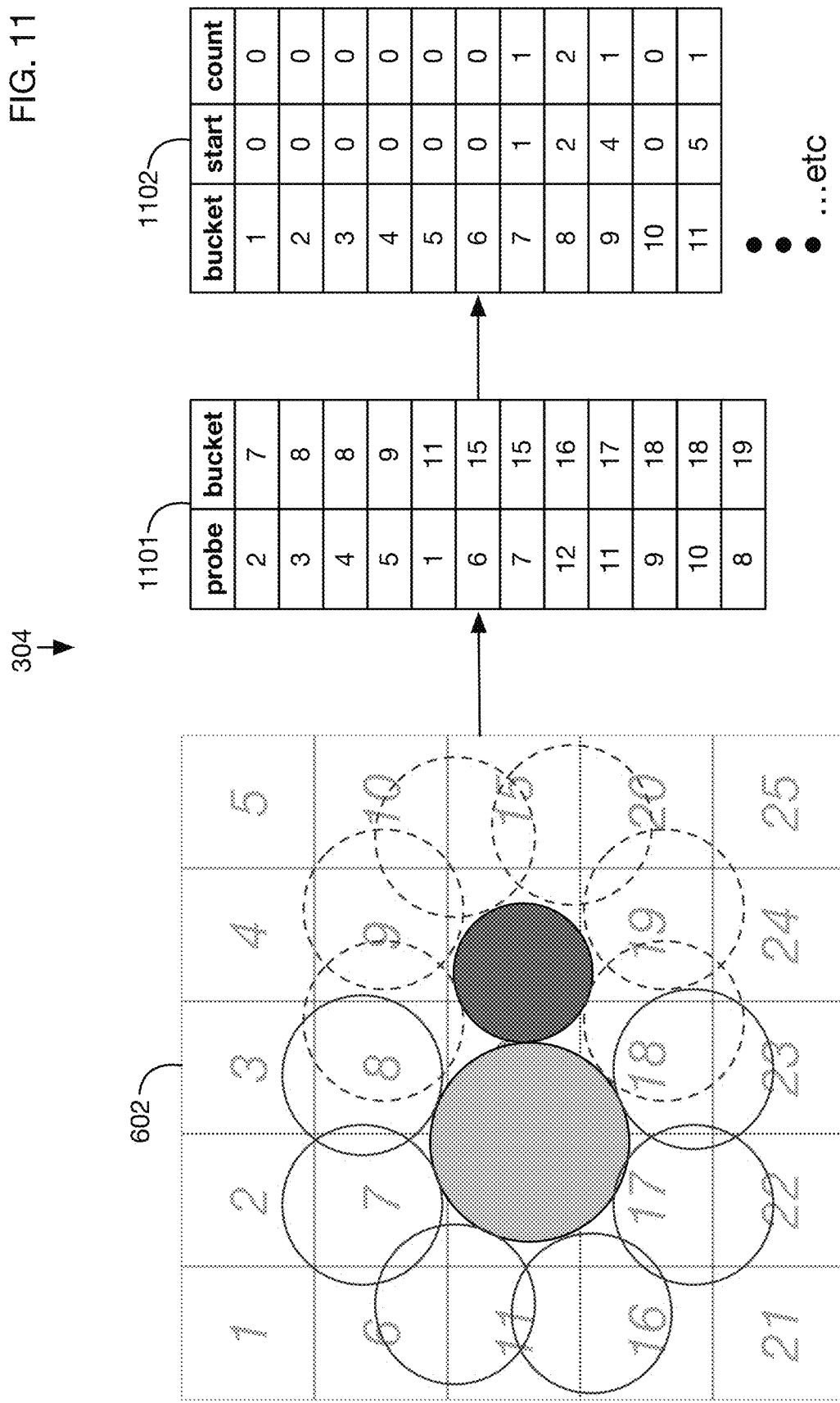
FIG. 11 illustrates spatial bucketing of probes, similar to the spatial bucketing of atoms shown in FIG. 6.

After the final list of probes 1010 is generated, by removing probes that overlap with atoms, the probes may be placed into spatial buckets in operation 304, which is illustrated in FIG. 11. This operation is analogous to the step 301 to place atoms into spatial buckets, which is shown in FIG. 6. For ease of illustration the same grid of buckets 602 is shown in FIG. 11 for the probes; one or more embodiments may use either the same or different buckets for atoms and for probes. The probes 1010 are mapped to buckets and the list 1101 is sorted by bucket. An index 1102 may be generated to support fast retrieval of the probes in each bucket. These operations may be parallelized on a GPU across probes. For example, list 1101 may be sorted by bucket on a GPU using a radix sort.

The next step in construction of the surface is to define and calculate a spatial field from which the desired surface can be obtained. The solvent-excluded surface will be the isosurface of the spatial field at the zero value. Conceptually the spatial field will measure how far a point is from the desired solvent-excluded surface, which is the atom-facing "inner" side of the probes' surfaces. It will be defined as a signed distance from the inner side of the probe surface, with the sign set to positive on the "atom side" and negative on the "probe side."

Figure 12B:
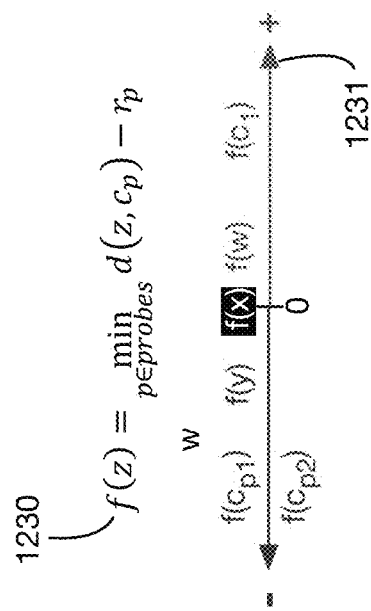
FIGS. 12A and 12B illustrate a framework for locating the solvent excluded surface as the zero isosurface of a function that measures the distance to the closest probe surface.
Figure 12A:
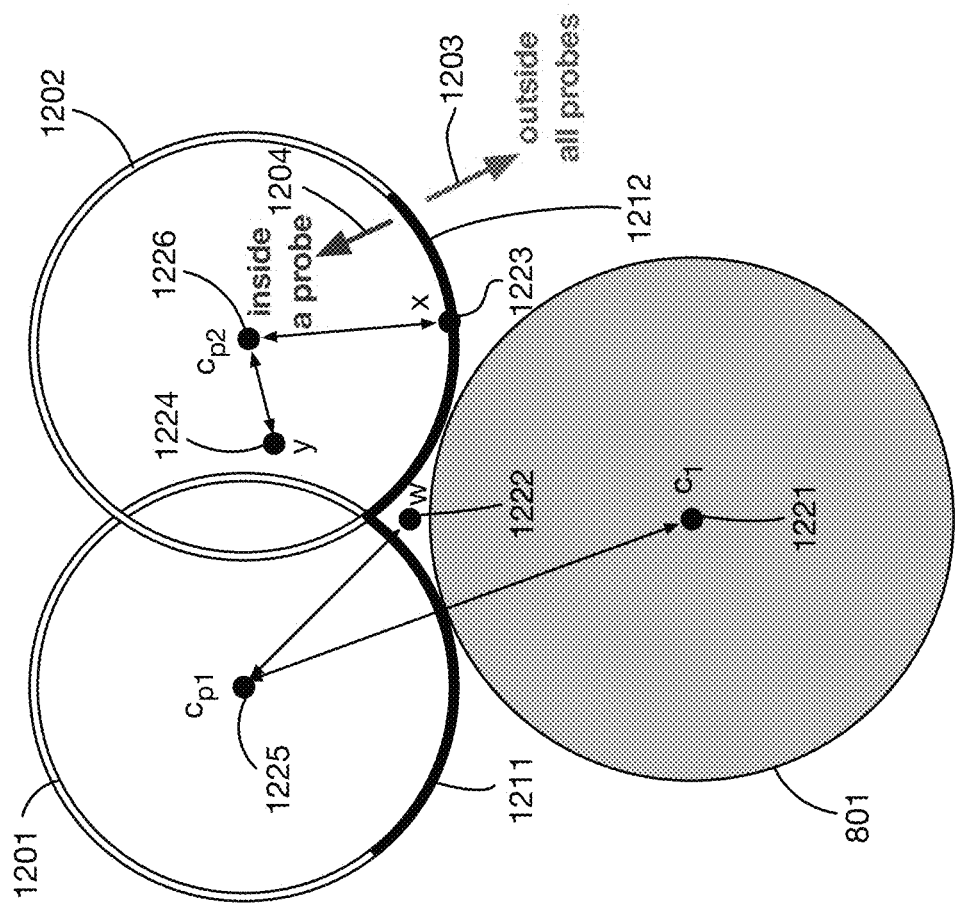

FIGS. 12A and 12B illustrate a preliminary step in constructing an appropriate spatial field. For ease of illustration, we show only a single atom 801 and two probes 1201 and 1202. The desired portion of the solvent-excluded surface is the atom-facing section 1211 of the surface of probe 1201 and the atom-facing section 1212 of the surface of probe 1202. These surface portions 1211 and 1212 partition the space into an "outside" region 1203 and an "inside" region 1204. The spatial field should have a positive value in the outside region, a negative value in the inside region, and a zero value on the surfaces 122 and 1212. A preliminary function that has these features is function 1230, which measures the minimum distance between a point and a probe center, less the probe radius. This function is positive for a point that is outside all probes, and is negative for a point that is inside one or more probes. FIG. 12A shows illustrative points in the space; FIG. 12B shows the value of function 1230 at these points on number line 1231, with positive values shown in red, negative values shown in blue, and zero values shown in white. The center 1221 of atom 801 has a positive value, because it is outside all probes. The center of any atom will be outside all probes, because the distance to a probe center is at least the atom radius plus the probe radius; hence the function 1230 will be positive at each atom center. The point 1222 has a positive value because it is outside both probes 1201 and 1202. Point 1223 on the surface 1212 has a zero value, as desired. Point 1224 has a negative value because it is inside probe 1202. The centers 1225 and 1226 of probes 1201 and 1202 have negative values. Any probe center will have a negative value because the value of function 1230 at a probe center is the negative of the probe radius.

Figure 13:
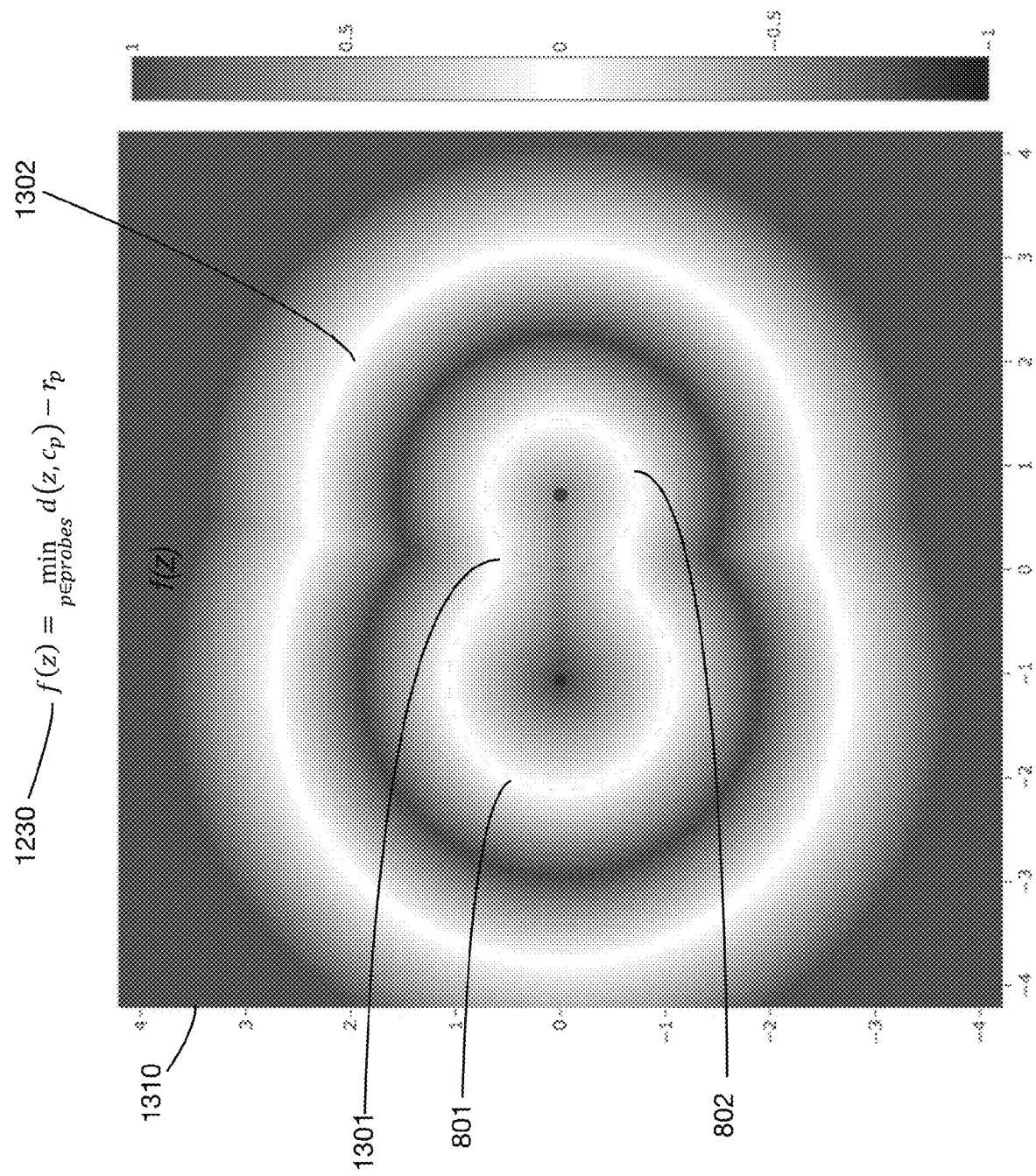
FIG. 13 shows a spatial field generated by the function of FIG. 12B; the zero isosurface does locate the solvent-excluded surface but also includes another surface on the outside surfaces of the probes.

FIG. 13 shows a "heat map" 1310 that illustrates the spatial field of function 1230 for the example molecule consisting of atoms 801 and 802. Positive values of the spatial field are shaded red, negative values are shaded blue, and zero values are shaded white. This heat map shows that the desired solvent-excluded surface is a zero isosurface 1301. For the function 1230, there is a second zero isosurface 1302 on the non-atom facing portion of the probe surfaces. One or more embodiments may process the spatial field 1310 to select only the inner isosurface 1301 as the solvent-excluded surface. The outer surface 1302 may also be generated by one or more embodiments as it may be useful for certain analyses or molecular visualizations.

Figure 14B:
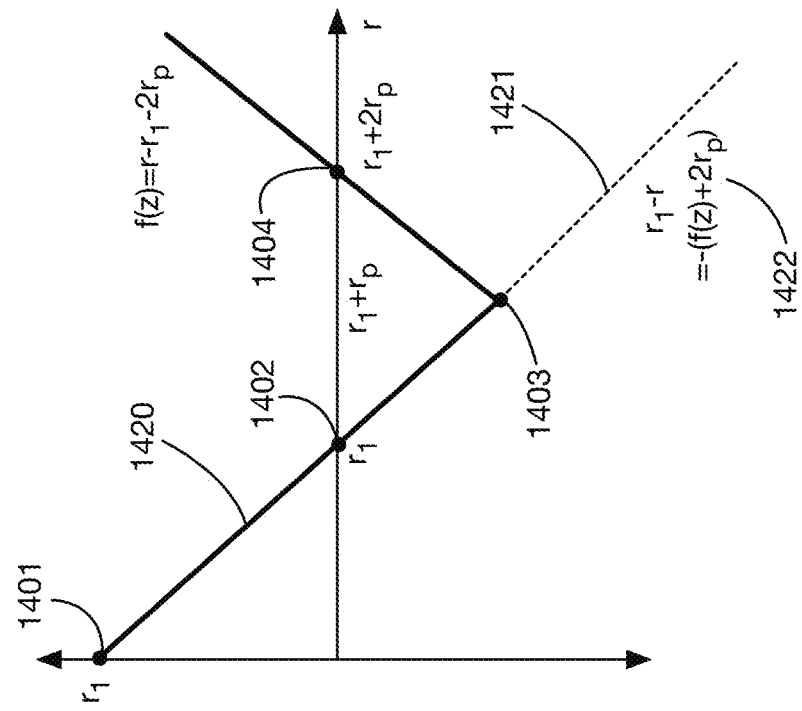
FIGS. 14A and 14B illustrate the reason that the function of 12B generates two isosurfaces, and shows a correction to this function to address this issue.
Figure 14A:
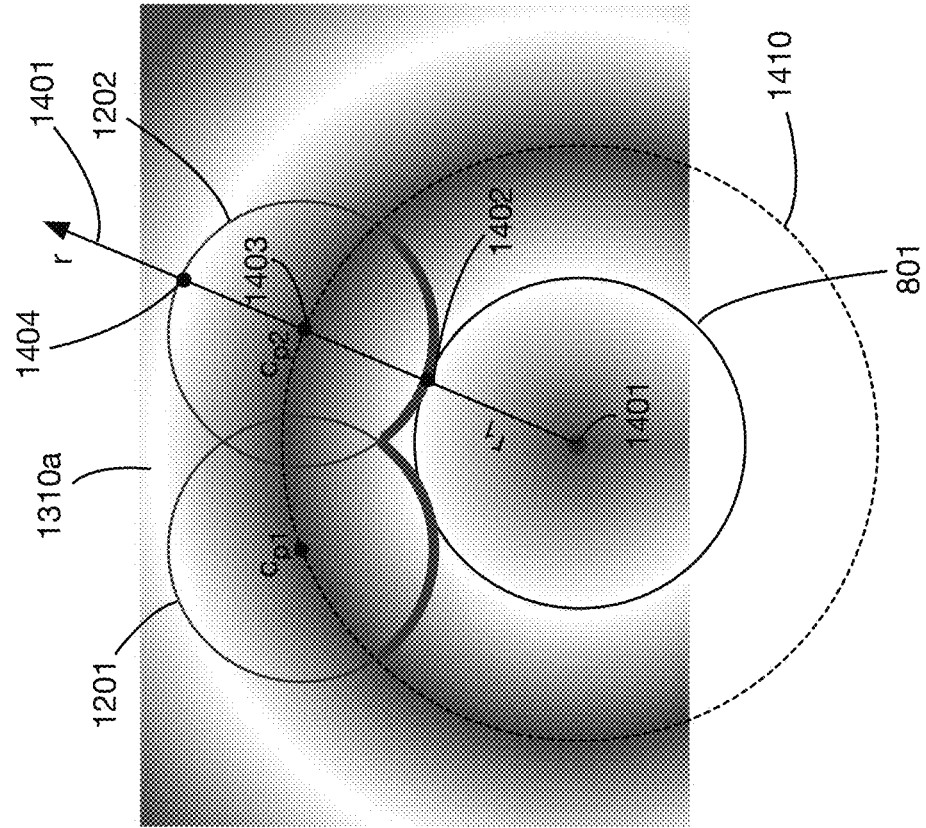
Figure 15:
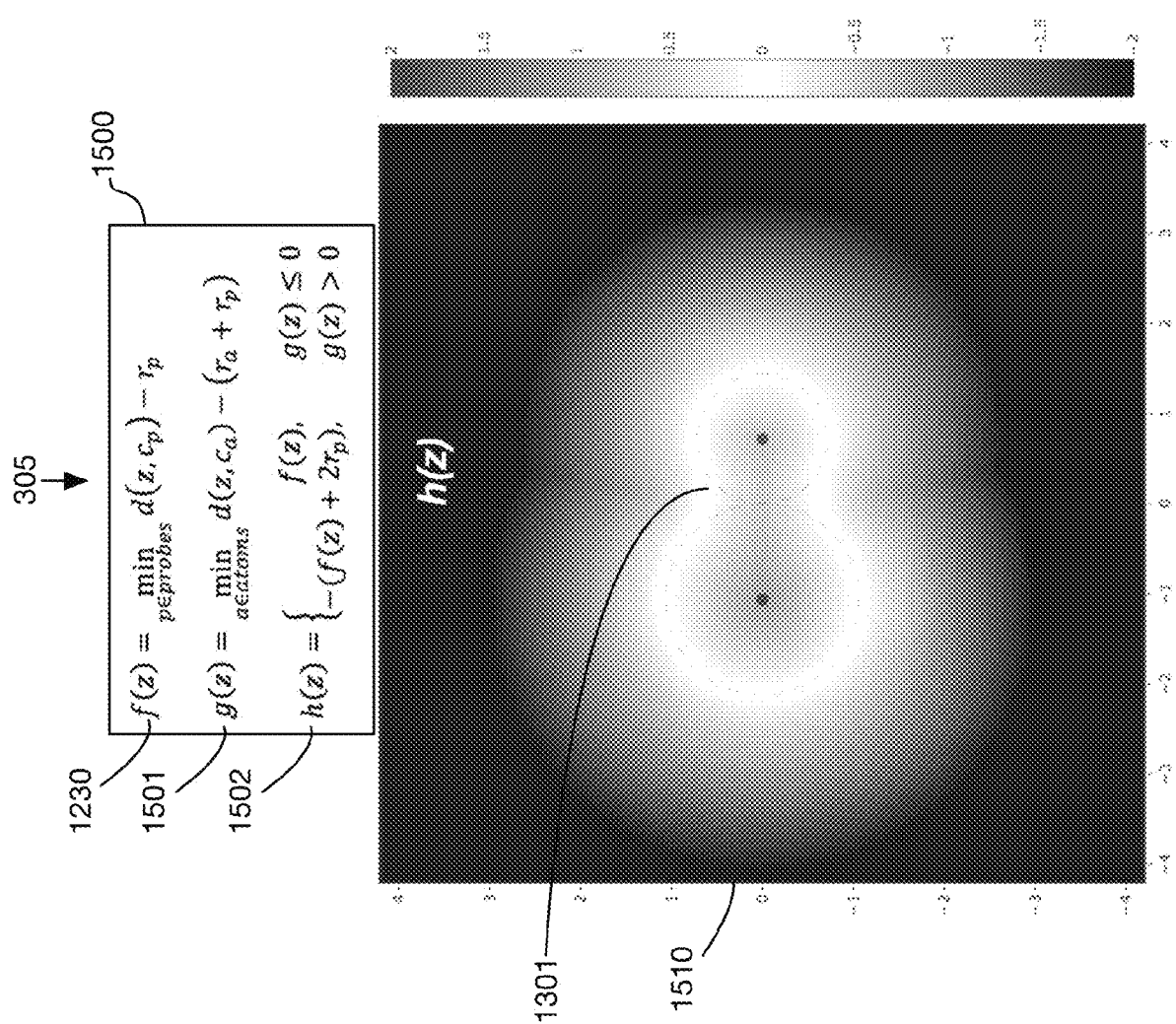
FIG. 15 shows the corrected function of FIG. 14B and the resulting isosurface.

FIGS. 14A, 14B, and 15 illustrate a method that may be used in one or more embodiments to adjust the function 1230 so that only the inner zero isosurface 1301 is present; this may simplify generation of the solvent-excluded surface in certain applications. FIG. 14A illustrates a heat map 1310a for function 1230 around a single atom 801. FIG. 14B shows a plot 1420 of the function 1230 along a ray 1401 from the center 1401 of atom 801 through the center 1403 of probe 1202, as a function of the distance r from the atom center 1401. At point 1401, plot 1420 has a positive value as expected. The function value declines to zero at point 1402 and to a negative value at the center 1403 of the probe. After point 1403, the plot 1403 begins to increase and crosses zero at point 1404, on the other non-atom-facing side of the probe surface. To modify the function 1230 to eliminate the outer zero isosurface, the function may be modified after point 1403 to continue its negative slope instead of turning upwards. This corner in the function occurs in general for points outside the "extended atom" sphere 1410 with radius equal to the atom radius plus the probe radius. As the plot 1420 indicates, inside the sphere 1410 the function value is $f(r)=r_1-r$, where $r_1$ is the radius of atom 801. Outside the sphere 1410 the function value is $f(r)=r-r_1-2r_p$, where $r_p$ is the radius of the probe. Therefore, the function may be modified with formula 1422 by adding $2r_p$ to its value and inverting it in the region outside extended atom sphere 1410. This generates segment 1421 of the function that avoids the corner at point 1403.

FIG. 15 shows the result of this modification in heat map 1510. The formulas 1500 illustrate the calculations that generate a function 1502 that is used for the spatial field. This function is equal to the previously described function 1230 for points that are inside any "extended atom sphere." Outside these extended atom spheres, the function is adjusted as described with respect to FIG. 14B. Function 1501 determines whether a point is inside or outside an extended atom sphere. The adjusted function 1502 has a single zero isosurface 1301, as desired, which is the solvent-excluded surface.

Figure 16:
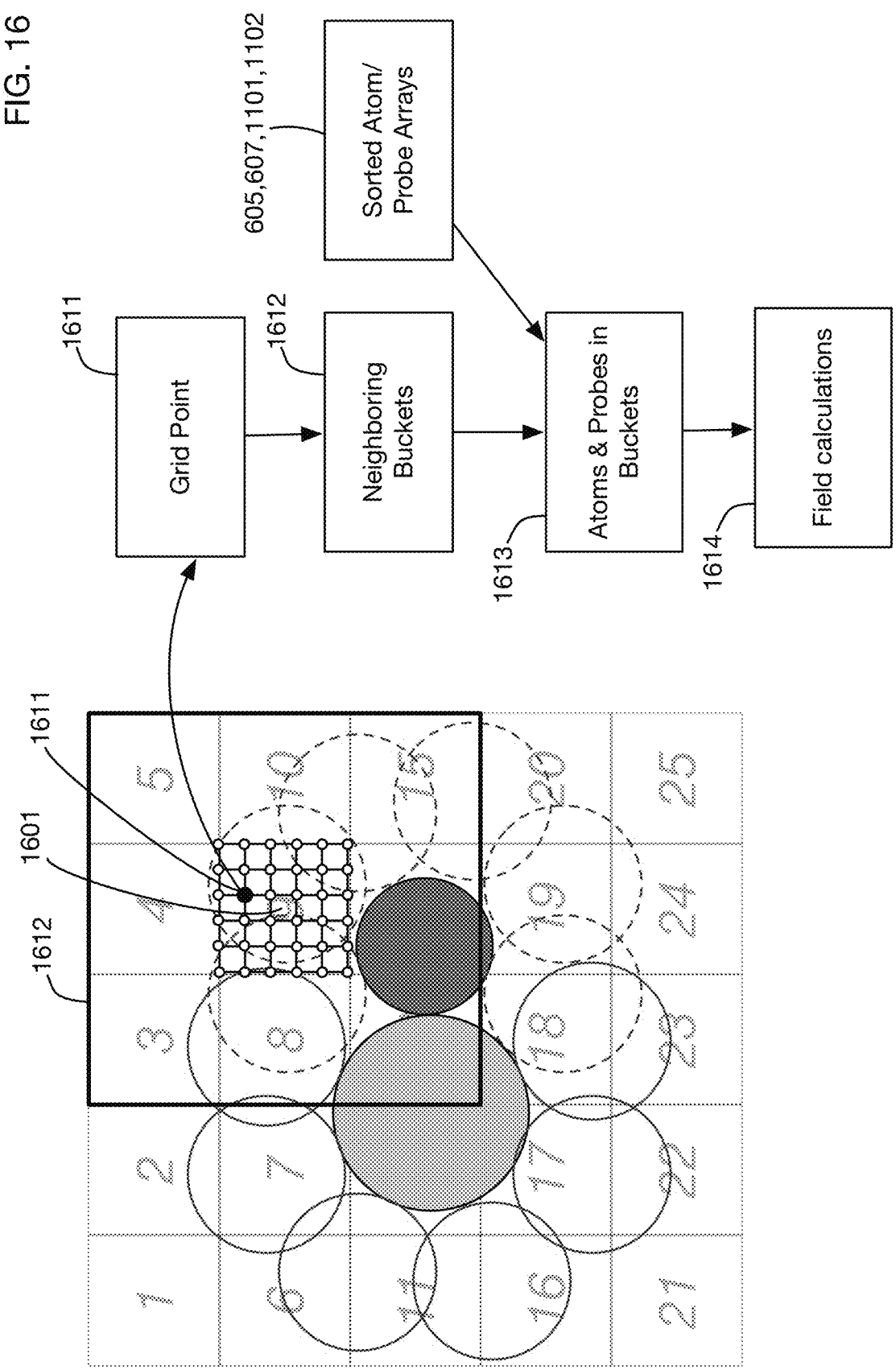
FIG. 16 illustrates a process for calculating a spatial field at discrete points on a grid.

FIG. 16 illustrates a method for generating the spatial field 1510 that may be used in one or more embodiments. A bounding volume (such as a box for example) may be calculated around the molecule and the probes, and a grid of points may be overlaid onto this bounding volume. The function may be evaluated at the points of the grid to provide an approximation of the spatial field. FIG. 16 shows a small portion 1601 of a grid of points in a region surrounding the atoms and probes of the running example molecule. Grid points such as point 1611 are obtained or generated from the grid. To optimize the calculation of values 1230 and 1501, which involve minimizing distances over probes and atoms, the neighboring buckets 1612 of grid point 1611 may be used along with the sorted atom and probe lists and related indices 605, 607, 1101, and 1102, to locate the atoms and probes 1613 in the vicinity of the grid point. These atoms and probes 1613 may then be used along with grid point 1611 to perform the spatial field calculations 1500. These calculations and steps may be parallelized over grid points since they are no dependencies among different grid points.

Figure 17:
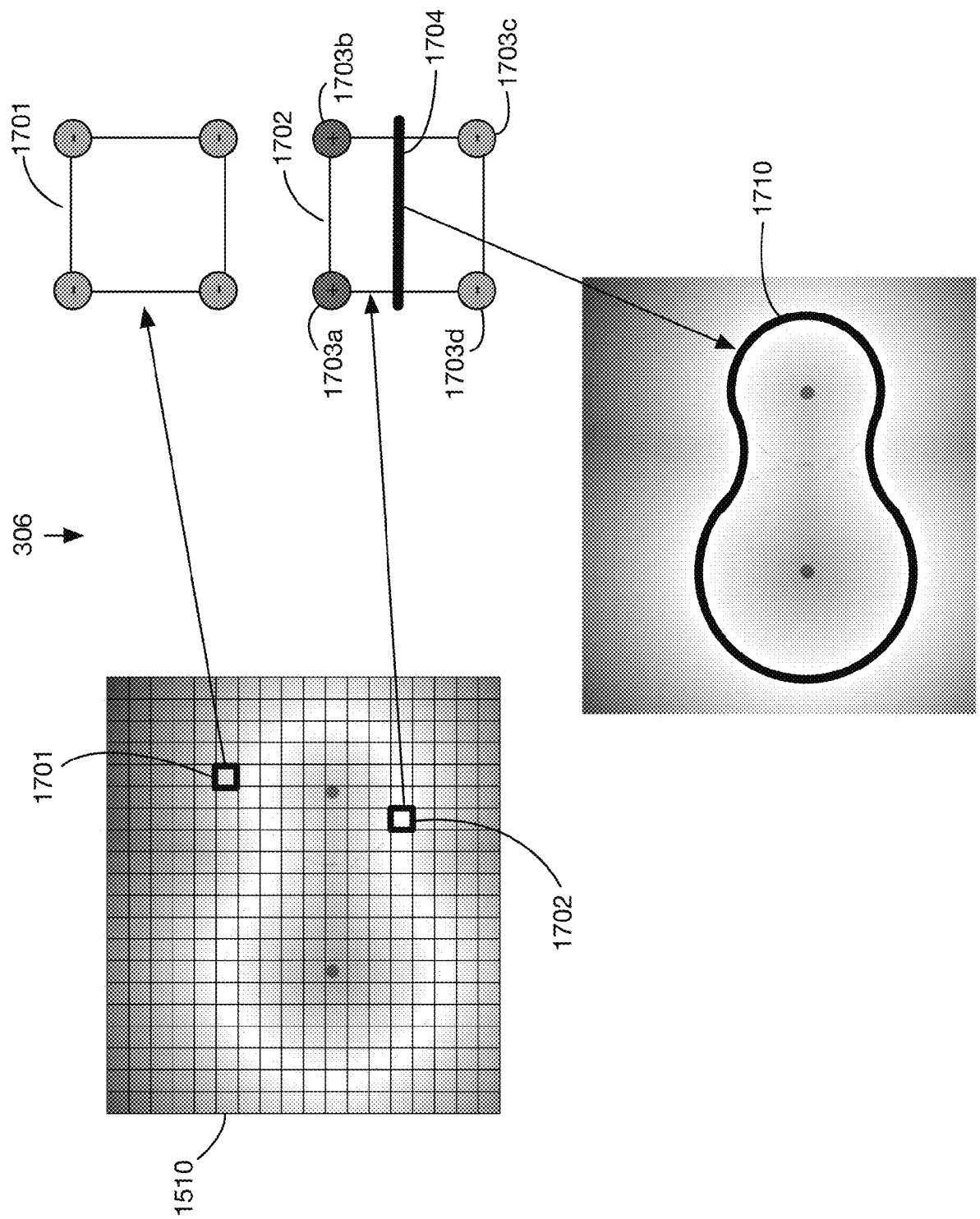
FIG. 17 illustrates a method for generating a zero isosurface from the grid point values calculated as shown in FIG. 17.

The final step 306 of generating the solvent-excluded surface as the zero isosurface of the spatial field is illustrated in FIG. 17. The bounding volume surrounding the molecule and the probes is partitioned into cells with corners at grid points. The cells may be for example cubical or tetrahedral, or in general may be any polyhedral shape. For each cell, the spatial field values at the corner grid points are used to determine whether the zero isosurface of the field passes through the cell, and if so where it intersects the cell. One or more embodiments may use for example a marching cubes algorithm or a variant thereof to locate the zero isosurface from the corner values of cubical cells. This process is illustrated in FIG. 17 with an array of cells overlaid onto spatial field map 1510. For cell 1701, the values of grid points at the four corners of the cell are all negative; hence the zero isosurface does not pass through this cell. For cell 1701, the spatial field value at corners 1703a and 1703b is positive, while the value at corners 1703c and 1703d is negative; hence the system determines that a portion 1704 of the zero isosurface passes through the cell. Determination of whether and where a zero isosurface passes through a cell may be parallelized over cells, for example on a GPU. The portions of the zero isosurface in cells such as 1704 are then combined to form the final solvent-excluded surface 1710. This surface may then be displayed as part of a molecular visualization system or molecular design system, or stored for future use.

Because of the parallelization possible with the steps described above, and because of other efficiencies due to spatial indexing of atoms and probes, embodiments of the invention may generate a solvent-excluded surface much more rapidly than many existing systems. This performance improvement is illustrated in FIG. 18. This figure shows benchmarks of the time to generate a solvent-excluded surface for molecules of various sizes (with models obtained from the Protein Data Bank). The surfaces for these molecules were generated using an embodiment of the invention, and using two common molecular visualization systems: Pymol™ and ChimeraX™. The plot is a log-log plot, so spacing between horizontal gridlines represents an order of magnitude (10×) difference in performance. Line 1801 shows performance of the embodiment of the invention; line 1802 shows performance of ChimeraX; and line 1803 shows performance of Pymol. The rightmost point on each line is performance on the largest molecule benchmarked 1804, which has 307,033 atoms. For this large molecule, the embodiment of the invention took 0.5 seconds to generate a solvent-excluded surface; Chimera took 35.3 seconds–a 70× difference, and Pymol took 161.5 seconds–a 320× difference. These benchmarks illustrate that embodiments of the invention may make a dramatic improvement in the time to generate a solvent-excluded surface. With embodiments of the invention, rapidly generating a solvent-excluded surface becomes practical even for large molecules, which may facilitate interactive exploration of molecules and interactive modification of molecular structures.

While the invention herein disclosed has been described by means of specific embodiments and applications thereof, numerous modifications and variations could be made thereto by those skilled in the art without departing from the scope of the invention set forth in the claims.

What is claimed is:

1. A system that rapidly generates a solvent-excluded surface, comprising:
   a processor;
   a memory coupled to said processor, wherein said memory comprises specific software instructions; and,
   a display coupled to said processor and to said memory;
   wherein said processor executes said specific software instructions, such that via said specific software instructions said processor is configured to
      obtain a 3D model of a molecule comprising a plurality of atoms, wherein each atom of said plurality of atoms comprises an atom center and an atom radius;
      obtain a probe radius;
      generate a plurality of vertices corresponding to each atom of said plurality of atoms, wherein each vertex of said plurality of vertices is on a sphere centered at said atom center, said sphere comprising a radius equal to said atom radius plus said probe radius;
      generate a plurality of probes comprising a sphere centered at each vertex of said plurality of vertices of each atom of said plurality of atoms, said sphere comprising a radius of said probe radius;
      test whether each probe of said plurality of probes intersects any atom of said plurality of atoms in more than one point;
      remove from said plurality of probes all probes that intersect any atom of said plurality of atoms in more than one point, to leave a plurality of final probes;
      define a 3D grid with a plurality of grid points that covers a volume containing said plurality of atoms and said plurality of final probes;
      for each grid point of said 3D grid, calculate a value of a spatial field at said each grid point, wherein
         said value comprises a minimum signed distance from said each grid point to an atom-facing portion of a surface of a probe of said plurality of final probes; and
         said spatial field at an atom center comprises an opposite sign from said spatial field at a probe center; and,
      generate a solvent-excluded surface of said molecule as a zero isosurface of said spatial field.

2. The system of claim 1, wherein said processor is further configured to display said solvent-excluded surface on said display.

3. The system of claim 1, wherein said plurality of vertices corresponding to said each atom comprise vertices of an icosphere.

4. The system of claim 1, wherein said processor generates said zero isosurface of said spatial field with a marching cubes algorithm.

5. The system of claim 1, wherein
   said processor is further configured to group said plurality of atoms into spatial buckets;
   said test whether each probe of said plurality of probes intersects any atom of said plurality of atoms in more than one point comprises
      identify a spatial bucket containing a center of said each probe;
      identify a group of spatial buckets equal to or near said spatial bucket;
      retrieve atoms in said group of spatial buckets; and,
      test whether said each probe intersects any atom of said atoms in said group of spatial buckets.

6. The system of claim 1, wherein said calculate said value of a spatial field at said each grid point comprises
   calculate a first value as a minimum of a distance between said each grid point and an atom center of an atom of said plurality of atoms less the atom radius of said atom and less said probe radius;
   calculate a second value as a minimum of a distance between said each grid point and a center of a probe of said plurality of final probes minus said probe radius;
   when said first value is negative or zero, set said value of said spatial field to said second value; and,
   when said first value is positive, set said value of said spatial field to a negative of a sum of said second value and twice said probe radius.

7. The system of claim 6, wherein
said processor is further configured to group said plurality of atoms and said plurality of final probes into spatial buckets;
said calculate said first value comprises identify a spatial bucket containing said each grid point;
identify a group of spatial buckets equal to or near said spatial bucket;
retrieve atoms in said group of spatial buckets; and,
set said first value to a minimum of a distance between said each grid point and an atom center of an atom of said atoms in said group of spatial buckets less the atom radius of said atom and less said probe radius; and, said calculate said second value comprises
identify a spatial bucket containing said each grid point;
identify a group of spatial buckets equal to or near said spatial bucket;
retrieve probes in said group of spatial buckets; and,
set said second value to a minimum of a distance between said each grid point and a center of a probe of said probes in said group of spatial buckets minus said probe radius.

8. The system of claim 7, wherein said group said plurality of atoms and said plurality of final probes into spatial buckets comprises
map each atom of said plurality of atoms to a bucket, to generate an atom-bucket list;
sort said atom-bucket list by bucket, to generate a sorted atom-bucket list;
generate a bucket-to-atoms index from said sorted atom-bucket list;
map each probe of said plurality of final probes to a bucket, to generate a probe-bucket list;
sort said probe-bucket list by bucket, to generate a sorted probe-bucket list; and,
generate a bucket-to-probes index from said sorted probe-bucket list.

9. The system of claim 1, wherein said processor comprises or is coupled to a parallel processing unit configured to execute computational tasks in parallel.

10. The system of claim 9, wherein said parallel processing unit comprises a GPU.

11. The system of claim 9, wherein said test whether each probe of said plurality of probes intersects any atom of said plurality of atoms in more than one point comprises a computational task executed on said parallel processing unit in parallel with one or more corresponding tests for one or more other probes of said plurality of probes, such that multiple probes of said plurality of probes are tested in parallel.

12. The system of claim 9, wherein said calculate a value of a spatial field at said each grid point comprises a computational task executed on said parallel processing unit in parallel with one or more corresponding calculations for one or more other grid points of said 3D grid, such that calculations for multiple grid points of said plurality of grid points are computed in parallel.

13. The system of claim 9, wherein said generate a solvent-excluded surface of said molecule as a zero isosurface of said spatial field comprises
partition said volume into a plurality of cells;
generate a computational task for each cell of said plurality of cells wherein said computational task comprises
calculate a portion of said zero isosurface that passes through said each cell, or
determine that no portion of said zero isosurface passes through said each cell; and,
execute said computational task for said each cell on said parallel processing unit in parallel with one or more corresponding computational tasks for one or more other cells of said plurality of cells, such that calculations for multiple cells of said plurality of cells are computed in parallel.

14. A system that rapidly generates a solvent-excluded surface, comprising:
a processor, wherein said processor comprises or is coupled to a parallel processing unit configured to execute computational tasks in parallel;
a memory coupled to said processor; and,
a display coupled to said processor and to said memory;
wherein said processor is configured to
obtain a 3D model of a molecule comprising a plurality of atoms, wherein each atom of said plurality of atoms comprises an atom center and an atom radius;
obtain a probe radius;
generate a plurality of vertices corresponding to each atom of said plurality of atoms, wherein each vertex of said plurality of vertices is on a sphere centered at said atom center, said sphere comprising a radius equal to said atom radius plus said probe radius;
generate a plurality of probes comprising a sphere centered at each vertex of said plurality of vertices of each atom of said plurality of atoms, said sphere comprising a radius of said probe radius;
test whether each probe of said plurality of probes intersects any atom of said plurality of atoms in more than one point;
remove from said plurality of probes all probes that intersect any atom of said plurality of atoms in more than one point, to leave a plurality of final probes;
define a 3D grid with a plurality of grid points that covers a volume containing said plurality of atoms and said plurality of final probes;
for each grid point of said 3D grid, calculate a value of a spatial field at said each grid point, wherein
said value comprises a minimum signed distance from said each grid point to an atom-facing portion of a surface of a probe of said plurality of final probes; and
said spatial field at an atom center comprises an opposite sign from said spatial field at a probe center; and,
generate a solvent-excluded surface of said molecule as a zero isosurface of said spatial field;
wherein
said test whether each probe of said plurality of probes intersects any atom of said plurality of atoms in more than one point comprises a computational task executed on said parallel processing unit in parallel with one or more corresponding tests for one or more other probes of said plurality of probes, such that multiple probes of said plurality of probes are tested in parallel;
said calculate a value of a spatial field at said each grid point comprises a computational task executed on said parallel processing unit in parallel with one or more corresponding calculations for one or more other grid points of said 3D grid, such that calculations for multiple grid points of said plurality of grid points are computed in parallel; and,
said generate a solvent-excluded surface of said molecule as a zero isosurface of said spatial field comprises
partition said volume into a plurality of cells;
generate a computational task for each cell of said plurality of cells
wherein said computational task comprises calculate a portion of said zero isosurface that passes through said each cell, or determine that no portion of said zero isosurface passes through said each cell; and, execute said computational task for said each cell on said parallel processing unit in parallel with one or more corresponding computational tasks for one or more other cells of said plurality of cells, such that calculations for multiple cells of said plurality of cells are computed in parallel.

15. The system of claim 14, wherein said calculate said value of a spatial field at said each grid point comprises calculate a first value as a minimum of a distance between said each grid point and an atom center of an atom of said plurality of atoms less the atom radius of said atom and less said probe radius;

calculate a second value as a minimum of a distance between said each grid point and a center of a probe of said plurality of final probes minus said probe radius;

when said first value is negative or zero, set said value of said spatial field to said second value; and, when said first value is positive, set said value of said spatial field to a negative of a sum of said second value and twice said probe radius.

16. The system of claim 15, wherein said processor is further configured to group said plurality of atoms and said plurality of final probes into spatial buckets;

said test whether each probe of said plurality of probes intersects any atom of said plurality of atoms in more than one point comprises identify a spatial bucket containing a center of said each probe;

identify a group of spatial buckets equal to or near said spatial bucket;

retrieve atoms in said group of spatial buckets; and, test whether said each probe intersects any atom of said atoms in said group of spatial buckets;

said calculate said first value comprises identify a spatial bucket containing said each grid point;

identify a group of spatial buckets equal to or near said spatial bucket;

retrieve atoms in said group of spatial buckets; and, set said first value to a minimum of a distance between said each grid point and an atom center of an atom of said atoms in said group of spatial buckets less the atom radius of said atom and less said probe radius; and, said calculate said second value comprises identify a spatial bucket containing said each grid point;

identify a group of spatial buckets equal to or near said spatial bucket;

retrieve probes in said group of spatial buckets; and, set said second value to a minimum of a distance between said each grid point and a center of a probe of said probes in said group of spatial buckets minus said probe radius.

17. The system of claim 16, wherein said processor is further configured to display said solvent-excluded surface on said display.

18. The system of claim 16, wherein said plurality of vertices corresponding to said each atom comprise vertices of an icosphere.

19. The system of claim 16, wherein said processor generates said zero isosurface of said spatial field with a marching cubes algorithm.

20. A system that rapidly generates a solvent-excluded surface, comprising:

a processor, wherein said processor comprises or is coupled to a GPU configured to execute computational tasks in parallel;

a memory coupled to said processor; and, a display coupled to said processor and to said memory;

wherein said processor is configured to obtain a 3D model of a molecule comprising a plurality of atoms, wherein each atom of said plurality of atoms comprises an atom center and an atom radius;

group said plurality of atoms into spatial buckets;

obtain a probe radius;

generate a plurality of vertices corresponding to each atom of said plurality of atoms, wherein each vertex of said plurality of vertices is on an icosphere centered at said atom center, said icosphere comprising a radius equal to said atom radius plus said probe radius;

generate a plurality of probes comprising a sphere centered at each vertex of said plurality of vertices of each atom of said plurality of atoms, said sphere comprising a radius of said probe radius;

test whether each probe of said plurality of probes intersects any atom of said plurality of atoms in more than one point, comprising identify a spatial bucket containing a center of said each probe;

identify a group of spatial buckets equal to or near said spatial bucket;

retrieve atoms in said group of spatial buckets; and, test whether said each probe intersects any atom of said atoms in said group of spatial buckets;

remove from said plurality of probes all probes that intersect any atom of said plurality of atoms in more than one point, to leave a plurality of final probes;

group said plurality of final probes into spatial buckets;

define a 3D grid with a plurality of grid points that covers a volume containing said plurality of atoms and said plurality of final probes;

for each grid point of said 3D grid, calculate a value of a spatial field at said each grid point, comprising calculate a first value as a minimum of a distance between said each grid point and an atom center of an atom of said plurality of atoms less the atom radius of said atom and less said probe radius;

calculate a second value as a minimum of a distance between said each grid point and a center of a probe of said plurality of final probes minus said probe radius;

when said first value is negative or zero, set said value of said spatial field to said second value; and, when said first value is positive, set said value of said spatial field to a negative of a sum of said second value and twice said probe radius;

generate a solvent-excluded surface of said molecule as a zero isosurface of said spatial field using a marching cubes algorithm; and, display said solvent-excluded surface on said display;

wherein said test whether each probe of said plurality of probes intersects any atom of said plurality of atoms in more than one point comprises a computational task executed on said GPU in parallel with one or more corresponding tests for one or more other probes of said plurality of probes, such that multiple probes of said plurality of probes are tested in parallel;

said calculate a value of a spatial field at said each grid point comprises a computational task executed on said GPU in parallel with one or more corresponding calculations for one or more other grid points of said 3D grid, such that calculations for multiple grid points of said plurality of grid points are computed in parallel; and, said generate a solvent-excluded surface of said molecule as a zero isosurface of said spatial field using a marching cubes algorithm comprises
partition said volume into a plurality of cubes;
generate a computational task for each cube of said plurality of cubes
wherein said computational task comprises
calculate a portion of said zero isosurface that passes through said each cube, or
determine that no portion of said zero isosurface passes through said each cube; and,
execute said computational task for said each cube on said GPU in parallel with one or more corresponding computational tasks for one or more other cubes of said plurality of cubes, such that calculations for multiple cubes of said plurality of cubes are computed in parallel.

* * * * *